US011484247B2

(12) United States Patent
Dascalu

(10) Patent No.: US 11,484,247 B2
(45) Date of Patent: Nov. 1, 2022

(54) PHONODERMOSCOPY, A MEDICAL DEVICE SYSTEM AND METHOD FOR SKIN DIAGNOSIS

(71) Applicant: BOSTEL TECHNOLOGIES, LLC, Braintree, MA (US)

(72) Inventor: Avi Dascalu, Tel Aviv (IL)

(73) Assignee: Bostel Technologies, LLC, Braintree, MA (US)

( * ) Notice: Subject to any disclaimer, the term of this patent is extended or adjusted under 35 U.S.C. 154(b) by 78 days.

(21) Appl. No.: 16/311,372

(22) PCT Filed: Jun. 26, 2017

(86) PCT No.: PCT/US2017/039189
§ 371 (c)(1),
(2) Date: Dec. 19, 2018

(87) PCT Pub. No.: WO2018/005316
PCT Pub. Date: Jan. 4, 2018

(65) Prior Publication Data
US 2019/0231249 A1 Aug. 1, 2019

Related U.S. Application Data

(60) Provisional application No. 62/357,394, filed on Jul. 1, 2016.

(51) Int. Cl.
*A61B 5/00* (2006.01)

(52) U.S. Cl.
CPC ............ *A61B 5/444* (2013.01); *A61B 5/0095* (2013.01); *A61B 5/7264* (2013.01); *A61B 5/746* (2013.01);
(Continued)

(58) Field of Classification Search
CPC ..... A61B 5/444; A61B 5/0095; A61B 5/7264; A61B 5/746; A61B 5/445; A61B 5/6898;
(Continued)

(56) References Cited

U.S. PATENT DOCUMENTS 6,215,893 B1 4/2001 Leshem et al.
2004/0077950 A1* 4/2004 Marshik-Geurts ... A61B 5/0086
600/475
(Continued)

FOREIGN PATENT DOCUMENTS

WO WO2006114003 11/2006
WO WO2011087807 A2 7/2011

OTHER PUBLICATIONS

Wikipedia, K-means clustering, 2008 (Year: 2008).*
(Continued)

*Primary Examiner* — Mark Roz
(74) *Attorney, Agent, or Firm* — Tristan A. Fuierer; Casimir Jones, S.C.

(57) ABSTRACT

The present invention provides for a new system and method for diagnosing skin cancer that provides for a more effective analysis of changes in skin tissue due to the duality of acquiring visual data and transforming such visual into an audio signal. The conversion of complicated patterns of visual information of a skin lesion by a computer aided classification analysis into diagnostic sounds results in a much higher resolution rate and increased precision of diagnosis.

15 Claims, 22 Drawing Sheets

(52) U.S. Cl.
CPC .............. *A61B 5/445* (2013.01); *A61B 5/6898* (2013.01); *A61B 5/7267* (2013.01); *A61B 5/742* (2013.01); *A61B 5/7405* (2013.01)

(58) Field of Classification Search
CPC ..... A61B 5/7267; A61B 5/7405; A61B 5/742; G06T 7/0012; G06T 7/0079–0097; G06K 9/0014; G06K 9/00234; G06K 9/3233–3266; G06K 9/34–348; G06K 9/6218–6226
See application file for complete search history.

(56) References Cited

U.S. PATENT DOCUMENTS

| | | | |
|---|---|---|---|
| 2005/0248474 A1* | 11/2005 | Wiser | H04S 7/40 341/50 |
| 2006/0120608 A1 | 6/2006 | Luo et al. | |
| 2006/0269111 A1* | 11/2006 | Stoecker | G16H 50/20 382/128 |
| 2009/0316970 A1* | 12/2009 | Kemper | G06T 7/0012 382/131 |
| 2010/0111392 A1* | 5/2010 | Valadez | G06T 7/0012 382/131 |
| 2012/0008838 A1* | 1/2012 | Guyon | G06T 7/62 382/128 |
| 2012/0136255 A1 | 5/2012 | Fan et al. | |
| 2012/0185418 A1 | 7/2012 | Thales | |
| 2013/0102877 A1 | 4/2013 | Mori et al. | |
| 2014/0036054 A1 | 2/2014 | Zouridakis | |
| 2015/0055855 A1 | 2/2015 | Rodriguez et al. | |
| 2016/0322066 A1 | 11/2016 | Sharifi et al. | |
| 2019/0053760 A1* | 2/2019 | Gerald, II | A61B 5/055 |
| 2019/0102878 A1* | 4/2019 | Zhang | G06N 3/0454 |

OTHER PUBLICATIONS

Szegedy ("Going Deeper With Convolutions", CVPR 2015) (Year: 2015).*
Nasa.gov, The Electromagnetic Spectrum (Year: 2013).*
Annessi, G. et al. Sensitivity, specificity, and diagnostic accuracy of three dermoscopic algorithmic methods in the diagnosis of doubtful melanocytic lesions: the importance of light brown structureless areas in differentiating atypical melanocytic nevi from thin melanomas. *J Am Acad Dermatol.* (May 2007); 56(5): 759-67.
Campos-do-Carmo, G. et al. Dermoscopy: basic concepts. *Int J Dermatol.* (Jul. 2008) ; 47(7): 712-9.
Eggermont, A.M. et al. Cutaneous melanoma. *Lancet.* (Mar. 1, 2014); 383(9919): 816-27.
Ferris, L.K. et al. New diagnostic aids for melanoma. *Dermatol Clin.* (Jul. 2012); 30(3): 535-545.
Mayer, J.E. et al. Screening, early detection, education, and trends for melanoma: Current status (2007-2013) and future directions: Part I. Epidemiology, high-risk groups, clinical strategies, and diagnostic technology. *Journal of the American Academy of Dermatology,* (Oct. 2014) 71:4: 599. e1-e12.
Noor, O. et al. A dermoscopy survey to assess who is using it and why it is or is not being used. *Int J Dermatol.* (Sep. 2009); 48(9): 951-2.
Russo, T. et al. Dermoscopy of Malignant Skin Tumours: What's New? *Dermatology* (2017) 233—:64-73.
Siegel, R. et al. Cancer statistics, 2012. CA *Cancer J Clin.* (Jan.-Feb. 2012); 62(1): 10-29.
Tsao, H. et al. Early detection of melanoma: reviewing the ABCDEs. American Academy of Dermatology Ad Hoc Task Force for the ABCDEs of Melanoma, *J Am Acad Dermatol.* (Apr. 2015) 72(4): 717-23.
Zortea, M. et al. Automatic learning of spatial patterns for diagnosis of skin lesions, 32$^{nd}$ Annual International Conference of the IEEE EMBS, Buenos Aires, Argentina, Aug. 31-Sep. 4, 2010.
Extended European Search Report, corresponding to European Patent Application No. 17820991.2, dated Mar. 6, 2020.

* cited by examiner

Figure 6 A and B

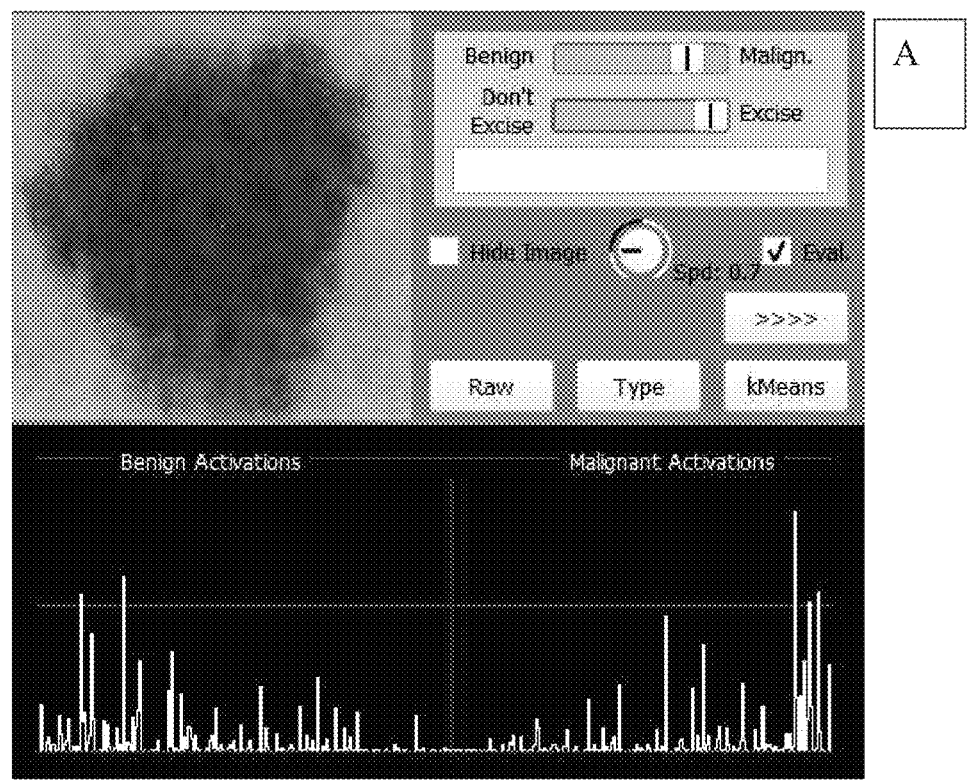
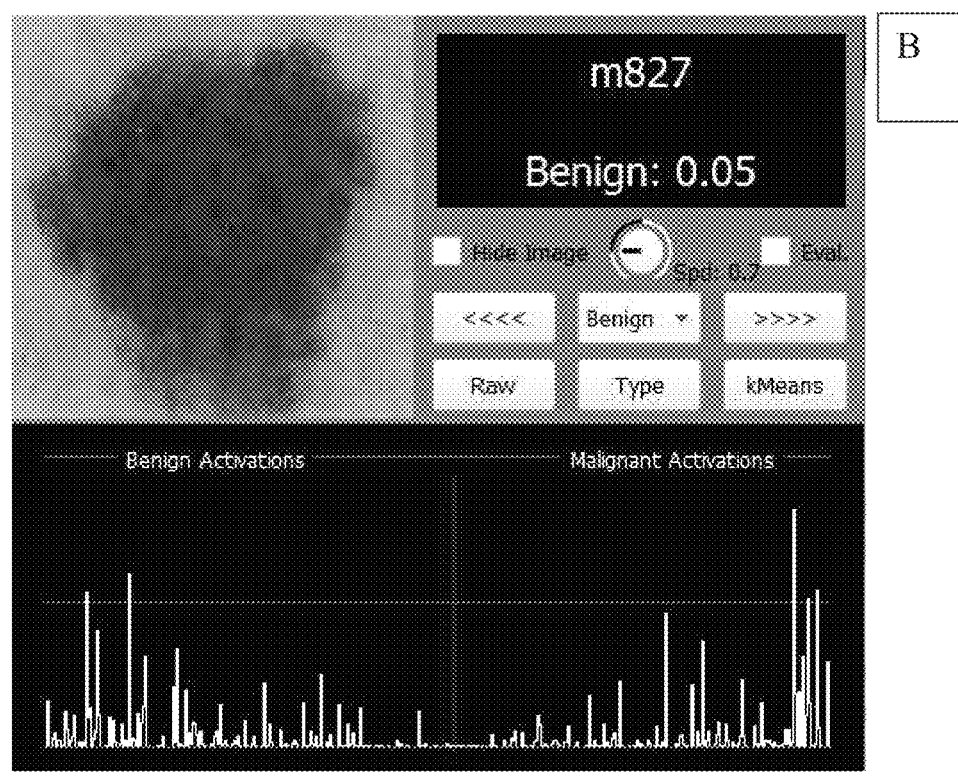
Figure 17

PHONODERMOSCOPY, A MEDICAL DEVICE SYSTEM AND METHOD FOR SKIN DIAGNOSIS

CROSS REFERENCE TO RELATED APPLICATION

This application is filed under the provisions of 35 U.S.C. § 371 and claims the priority of International Patent Application No. PCT/US2017/039189 filed on Jun. 26, 2017 which in turn claims priority to U.S. Provisional Patent Application No. 62/357,394 filed on Jul. 1, 2016, the contents of which are incorporated by reference herein for all purposes.

BACKGROUND OF THE INVENTION

Field of the Invention

The present invention provides for a system and method for the diagnosis of skin cancer. Pre-cancerous and/or other atypical skin lesions, including atypical moles, more specifically for a system and method for acquiring visual data from a skin lesion by a passive or active optical, electronical, thermal or mechanical method, processing the acquired visual field image into a classifier, applying a dermoscopic classification analysis to the image and converting, by sonification techniques, the data to an audio signal, assigning different audio patterns to each visual pattern, thereby enhancing the visual data by audio signal and increasing the precision of diagnosis.

Related Art

Malignant melanoma is a deadly cancer, claiming globally about 160.000 new cases per year and 48,000 deaths [1]. The incidence rate for melanoma between 1950 and 2007 rose more than 17-fold in men (1.9 to 33.5 per 100,000) and more than 9-fold in women (2.6 to 25.3 per 100,000) [2]. It is estimated that 76,000 new cases and 10,000 deaths (2017) are diagnosed each year and in the United State there is a lifelong probability of 1:36 for developing this cancer [3].

Generally, melanoma starts de novo in about 70% of subjects, with a small superficial skin lesion which, if left undiagnosed, might develop into a more advanced stage cancer, followed by silent lymph node spreading and invasion of vital organs such as liver and brain. Melanoma is staged by either direct invasion into the skin, the Breslow scale in mm, or by its skin level involvement, a Clark 1-5 structural skin level of involvement. Both are predictors of long term survival, which is almost unchanged at a Breslow depth beneath 1 mm and much decreased beyond Clark III stage. Therefore, early detection of melanoma, generally tagged as small melanoma, is critical.

The following different methods and diagnostic means for detection of the cutaneous melanoma are currently employed as a means of diagnosis although not always effective.

Visual recognition by an ABCDE rule which is 30 year old methodology that assesses Asymmetry, Border, Color, Diameter and Evolvement. It is used by about 40% of US dermatologists who refrain from the use of Epiluminescence microscopy [4], the golden standard of evaluation. The abovementioned ABCDE rule was reviewed in 2015 [5] and teaches the use of a diameter greater than 6 mm as a criteria for melanoma recognition. Consequently, it does not contribute to early detection of a melanoma. An attempt to change the diameter criteria, i.e. a decrease in the postulated 6 mm diameter leads to a major decrease in sensitivity and specificity, rendering the ABCDE ineffective for early melanoma detection. It is concluded that ABCDE visual criteria, although widely used, is a non-effective prevention method due to their innate criteria which misses the evolving melanomas, since all melanomas start as small melanomas.

Epiluminescence microscopy is a 65 years old art, which is considered the golden standard of evaluation. It is highly dependent on the skills and knowledge of the diagnostician. Epiluminescence microscopy is the bridge between clinical observation and histopathological diagnosis. It allows visualization of skin pigments up to the papillary dermis and improves detection sensitivity and specificity. Analysis is made by a clinician based on dermoscopy rules [6], which are based on a complicated dermoscopic pattern analysis. However, dermoscopy is physically challenging, since it requires a brief period of complete standstill of both physician and patient, allowing dermoscope optical focus on the skin lesion. During these few seconds of standstill the clinician is expected to recall data from a cluster of clinical signs and correlations, integrate all signs and make a decision on spot, based on past experience as compared to biopsies outcomes, a challenging task.

Complete dermoscopic pattern analysis of a lesion is the mainstream of diagnosis. It requires recognition of at least six different colors, representative of different pathological structural elements. In addition, there are at the very least nineteen different structural patterns recognizable based on the abovementioned colors, with additional pathogenic features of vascularization (six patterns) and specific location such as face (three patterns) and palmoplantar features (five patterns). Moreover, each of the dermoscopic patterns can diverge in extent, diameter, general or local appearance, or evolve as multi patterns with various area of expression on the same lesion and rendering the diagnosis beyond an encyclopedic task [7].

Due to the complexity of the dermoscopic pattern analysis method, different modifications have been proposed, such as a simplified ABCD rule, an intermediate seven rules assessment and an eleven rules checklist. The myriad of data and its interpretation render even experts in dermoscopy to identify melanomas with a relative low ratio from 5:1 to 15:1, i.e. the number of biopsies of benign lesions performed in order to make the diagnosis of one skin melanoma [8]. Furthermore, there are claims that one diagnostic sign might be more sensitive than other signs [9]. Observations of pattern recognition are delivered to higher brain functions that human beings are notorious for failing and not being able to determine a moderate effect of color on pattern recognition and/or having a limited capacity for processing information [10, 11]. Dermatologists follow the mental rule and commonly fail in diagnosing early small melanoma which is the critical period of growth of the tumor and most efficacious prevention [12]. Particularly, it was published that in a 59 series of patients, dermatologists (n=26) asked to identify 1 melanoma out of 4 images from the same patient. Statically, such a design confers a 25% chance of success to a random choice decision. Dermatologists rated at a mean 40% specificity (range from 19% to 63%), a number barely superior to chance [13].

Visual recognition by total body photography is a non-standardized methodology, a time consuming and patient expensive procedure. It uses the human comparison assessment and is subjected to biases of pixel photo during performance of the measurement, due to lighting, background and camera position [14]. The addition of patient assessment by artificial intelligence, an analysis based on computer evaluation of different colorimetric and geometric parameters of a lesion in real time, does not confer any advantage, yielding even more false positives compared to experienced or even inexperienced clinicians [15]. A wearable system that augments gross visual spectral changes through sonification [16] does not lead to any specific diagnosis of suspected skin cancer or melanoma due to the use of routine basic visual input as a diagnostic criteria, without processing data by any dermatologic rules. It involves and peruses visual shortcoming, bypassing the diagnostic signs of dermoscopical classification, does not capture a deeper dermoscopic image consisting of the in vivo evaluation of colors and microstructures of the epidermis, the dermoepidermal junction and the papillary dermis, which are not visible to the naked eye rendering the wearable methodology unproductive and its output irrelevant to nevi diagnosis.

Multispectrometry devices that provide measurements of melanin, collagen and hemoglobin with further use of image analysis, do not confer any advantage to epiluminescence microscopy [8]. Specific multispectral devices that assess melanin by adding to imaging a dermoscopic pattern analysis did not confer a convincing advantage. Although displaying a higher sensitivity, the specificity of these methodologies is considerably below that of simple epiluminescence microscopy in melanoma identification rate [8, 17]. Hence, such devices are approved for use as an assistance to morphological changes and although formerly approved did not gain popularity, especially due to the potential of missing the diagnosis [18].

Another group of skin malignancies, the Skin Cell Carcinomas, comprising of basal and squamous cell carcinomas, are the most common skin cancers [19, 20]. These are locally invasive tumors, rarely causing death but leading to major annoyance based on a need to treat. Their identification is likely biased by common means of diagnose.

Thus, due to the relative failure of current methods and apparatuses in identifying any type of skin cancers, especially early melanoma, it is highly desirable to identify a new system and method in order to diagnose all types of skin cancers.

SUMMARY OF THE INVENTION

The present invention provides a method to distinguish between cancerous and/or other pre-cancerous atypical tissue and non-cancerous tissue, specifically the difference between melanoma and non-melanoma type tissue. The present invention provides for a new system and method for diagnosing skin cancer that provides for a more effective analysis of changes in skin tissue due to the duality of acquiring visual data and transforming such visual into an audio signal. Surprisingly, the conversion of complicated patterns of visual information from a pattern analysis of a skin lesion into diagnostic sounds results in a much higher resolution rate and precision of diagnosis.

In one aspect, the present invention provides for a method of diagnosing skin cancer, the method comprising:
a. providing a tissue image of a tissue sample suspected of being cancerous;
b. generating a plurality of pixel segmentation of the tissue image, wherein each pixel segmentation is classified as specific type of tissue;
c. classifying each type of tissue by an associated Classifier to provide a plurality of classifier features based on shape, content and color;
d. introducing the plurality of classifier features into a Clustering algorithm to provide for centroides of data relating to the classifier features; and
e. applying an audio signal for each of the centroides of data, thereby providing for an audio output for diagnosing the tissue sample suspected of being cancerous.

In another aspect, the present invention provides for a method of evaluating a skin lesion for determining malignant or non-malignant tissue, method comprising:
providing a tissue image of the skin lesion;
generating segmentation of the tissue image, wherein similar types of tissue or features are grouped into one segment to provide a plurality of different segments comprising different types of tissue or features;
classifying each of the plurality of segments to provide a plurality of classified segments;
applying a clustering process to the classified segments to provide a plurality of clusters; and
applying a specific audio signal for each of the plurality of clusters to provide an audio output indicating either malignant or non-malignant tissue.

In yet another aspect, the present invention provides for a method of analyzing a tissue sample for determining suspected cancerous tissue, the method comprising:
a. providing a tissue image of the sample tissue;
b. transmitting the tissue image to a computer aided classification system;
c. extracting features from the tissue image with the computer aided classification system for classifying the tissue image, wherein extracted features characterize the sample tissue and such sample characterization is compared to characterization of a reference tissue to classify and provide classified features of the sample tissue;
d. applying an unsupervised clustering process to the classified features to provide a plurality of clusters; and
e. applying a specific audio signal for each of the plurality of clusters to provide an audio output to enhance identification of cancerous tissue.

In a still further aspect, the present invention a method for analysis and diagnosis of the presence of cancerous tissue, the method comprising:
a. applying electromagnetic or mechanical energy to skin tissue suspected of being malign;
b. capturing reflected and/or refracted electromagnetic or mechanical energy through a dermoscope or microscope;
c. converting the reflected and/or refracted or acquired energy into a visual image;
d. transmitting the input image to a classifier database;
e. generating a feature map by applying a deep learning classifier to the input image;
f. assigning dermoscopic patterns to the feature map generated by the classifier,
g. converting the dermoscopic patterns into an audio signal by use of a clustering algorithm selected from a supervised, unsupervised, reinforcement learning or combination thereof;
h. generating an audio signal from the output of the clustering algorithm, wherein the audio signal reflects the differences shown in the dermoscopic pattern; and
i. reviewing the audio signal to provide guidance for excising skin tissue suspected of being malign.

In another aspect the present invention provides a method for characterizing the difference between malignant and non-malignant skin tissue, the method comprising:
applying electromagnetic or mechanical energy to skin tissue suspected of being malign;

capturing reflected and/or refracted electromagnetic or mechanical energy through a dermoscope or microscope;

converting the reflected and/or refracted or acquired energy into a visual image; transmitting the input image to a classifier database;

generating a final feature map by applying deep learning techniques to the input image, such as analyzing the image through a convolutional neuronal network, for example, and combining data analysis by use of a known inception analysis architecture for computer vision, such as Inception v Networks (1,2,3 or 4);

assign dermoscopic patterns to the feature map generated by the classifier, either during image analysis or after analysis, in order to generate a discrete classification decision such as malignant vs. benign;

converting the feature map dermoscopic patterns into an audio signal by use of either of or a combination of supervised, unsupervised or reinforcement learning;

generating from the learning algorithm an audio signal which comprises different output sounds differentiated by frequency, duration, magnitude, spectrum, and spatial orientation and reflecting the differences shown in the dermoscopic pattern, as identified by their musical parallel of pitch, rhythm, tempo, dynamics and timbre; and converting the audio signal into an excise or do not excise guidance by audio and/or video means.

In another aspect, the present invention provides for a method of diagnosing the existence of onychomycosis, the method comprising:

a. providing a tissue image of a tissue sample suspected of being infected by a fungi;

b. generating a plurality of pixel segmentation of the tissue image, wherein each pixel segmentation is classified as specific type of tissue;

c. classifying each type of tissue by an associated Classifier to provide a plurality of classifier features based on shape, content and color;

d. introducing the plurality of classifier features into a Clustering algorithm to provide for centroides of data relating to the classifier features; and e. applying an audio signal for each of the centroides of data, thereby providing for an audio output for diagnosing the tissue sample suspected of being infected by fungi.

Importantly, the conversion of the dermoscopic pattern into an audio signal is preferably accomplished by a parameter mapping sonification method wherein a classification method and/or clustering algorithm is used to isolates clusters of data related to each tissue type and then assigned a unique sound to each tissue type. Such classification method may include but is not limited to raw weights classification, concept mapping classification and K-Means cluster analysis.

In a further aspect, the present invention provides for a non-invasive phonodermoscopy system for testing of skin tissue to determine cancerous effects, the system comprising:

a device for obtaining visual data of the skin tissue, wherein electromagnetic energy in infrared, visual and ultraviolet spectrum are applied to the skin tissue and refracted and/or reflected electromagnetic energy is captured to provide the visual data;

a processor operatively responsive to the visual data, wherein a computer aided classification method and a clustering algorithm segments different patterns of intensity and contrasts of tissue to provide an output cluster set;

an audio device to provide a specific audio signal output for each cluster in the output cluster set.

In yet another aspect, the present invention provides for a system to diagnose cancer of a skin lesion, the system comprising:

a unit for capturing electromagnetic waves from the skin lesion;

a direct input raw digital data visual screen communicatively connected to the unit for receiving captured electromagnetic waves from the skin lesion;

a visual data processing unit for converting the electromagnetic waves to a visual image;

a computer processor for processing classifier data and converting the visual image into classified data;

a dermoscopic pattern transduction analysis unit using a clustering program to convert classified data into a multiplicity of clusters;

a visual to audio transducer for converting the multiplicity of clusters into audio signals; and a headphone/speaker unit to provide an audio output of the audio signals to a subject.

In another aspect, the present invention provides for a method for examining an atypical skin lesion to determine whether to excise or not to excise the atypical skin lesion, the method comprising:

providing a tissue image of the atypical skin lesion;

generating segmentation of the tissue image, wherein similar types of tissue or features are grouped into one segment to provide a plurality of different segments comprising different types of tissue or features;

classifying each of the plurality of segments to provide a plurality of classified segments;

applying a clustering process to the classified segments to provide a plurality of clusters; and applying a specific audio signal for each of the plurality of clusters to provide an audio output to indicate if the atypical skin lesion is either malignant or non-malignant tissue thereby providing guidance to excise or not to excise the atypical skin lesion.

An atypical skin lesion includes lesions that are growing, spreading or pigmented, and/or those that occur on exposed areas of skin are of particular concern. Such lesions may include but is not limited to atypical melanocytic hyperplasia, atypical mole, dysplastic mole, cancerous skin diseases, actinic keratosis, basal and squamous cell carcinoma, etc.

Other features and advantages of the invention will be apparent from the following detailed description and claims.

BRIEF DESCRIPTION OF THE DRAWINGS

FIGS. 17A and B shows image and audio indication (bar graph of activations) of a malignant lesion wherein the results of pathology and audio sonification differ from classifier result.

DESCRIPTION OF THE INVENTION

Figure 1:
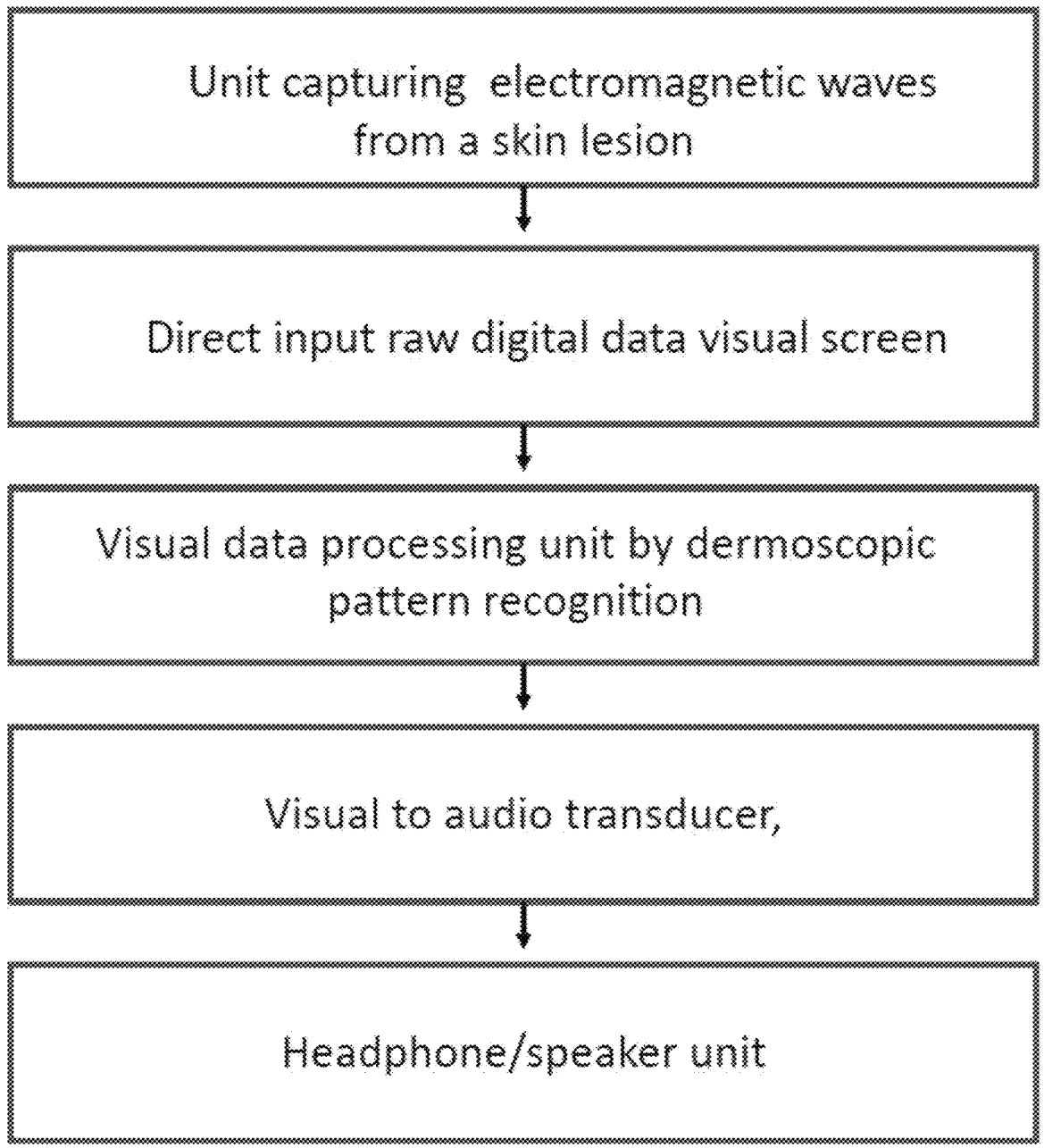
FIG. 1 shows a functional block diagram of a system and method for diagnosis by pattern analysis and sonification of data, according to one embodiment of the present invention.

The present invention provides for a medical device system and method for diagnosing skin lesions, or skin cancers, and particularly, skin tumors of melanocytic origin, i.e. malignant melanoma or non-melanocytic skin tumors, such as basal and squamous cell carcinoma. The present invention relates to a device which (i) acquires visual data from a skin lesion by an optical or mechanical method, or captures visual data by a sensor refracted electromagnetic waves such as UVA, visible spectrum or infrared wavelenghts or molecular vibrations, (ii) processing visual data to provide a visual field image; (iii) applies a dermoscopic pattern analysis to the acquired visual image and (iv) transforms the data into an audio signal, assigning different audio pitch, loudness, timbre, spatialization and temporal patterns of sound to each visual pattern, to be communicated through an algorithm to the practitioner; or directly applies to an acquired visual image by an available method or device a dermoscopic pattern analysis followed by audio signal transduction into specific diagnostic audio pitch, loudness, timbre, spatialization and temporal patterns.

An audio signal is important for further identification of the suspected cancerous tissue. Notably, the Calyx of Held, first described in 1893, is a giant glutamate secreting relay synapse in the auditory mammalian brainstem. It is involved in transduction of sound into neuronal activity and relatively fast transmission of auditory input [20]. Upon stimulation, sound waves transduction follow a mechanical process, lasting for about 1 ms, contrary to processing of visual stimuli, a photochemical operation lasting for about 50 ms [22]. Due to this at least 50 fold factor slower processing of visual input, auditory input can be quickly perceived and delivered to consciousness. Part of this delay for visual stimuli may be related to longer and slower neuronal pathways of delivering information to the cortex [23].

Thus, the sensitivity of the acoustic systems overcomes the vision system. If the audio and visual input are close to the perceiver, no brain compensation and adjustment of brain function are applied to, rendering a higher resolution rate and more stimuli identification for the acoustic signal than the visual function.

Data transformation into acoustic parameters which represent the acquired information, i.e. sonification, was used from the ancient Greek period and Medieval China to provide information of elapsed time. In the middle ages it was used by Kepler, finally contributing to his third law of planetary motion [24]. Sonification in various adaptations was used or proposed to be used, amongst others, as a highly perceptive substitute to visual information as apparatus providing warnings to pilots, device for monitoring architectural integrity of large structures, guiding the manipulation of surgical instruments during brain surgery, anesthesiology, analyzing seismology data, data display for the visually impaired, monitoring the oscillation of subatomic particles in quantum physics, fingerprint identification, skin pore audification by area and color distribution, training and rehabilitation, seizure detection in infants, optical coherence tomography monitoring, stroke rehabilitation [25, 26, 27, 28, 29].

As previously stated, cancers of the skin are the most common forms of cancer. There are several modalities [30], discussed hereinbelow, to assist with generating visual data and/or images for further sonification of data.

Photography is a technique that uses photographic devices to capture surface images of the skin in order to primarily identify suspicious and pigmented skin lesions. Polarized light photography relies on the fact that reflected light has two components, one regular reflectance to reflect the skin surface morphology, the other "back-scattered" from within the tissue. It is useful in the assessment of skin surface morphology when the proper polarizing filters and techniques are used.

Dermoscopy, also known as epiluminescence microscopy, uses handheld devices to show subsurface structures of the skin and optical light ray penetration beyond the skin surface and minimize surface reflection. Different types of dermoscopy include nonpolarized light contact dermoscopy that uses a nonpolarized light source such as a halogen light source and requires the use of an oil or gel to prevent surface reflection, attached directly to the skin mechanically. Additionally, dermoscopy can include the use of non-polarized dermoscopy devices that do not need a liquid interface and are equipped with a cross-polarized lens that absorbs scattered light waves. Polarized contact dermoscopy can attain the images of vascular and other structures. These devices are useful in visualizing melanin, blue nevi, and shiny white streaks. Still further, both devices can be combined.

Thermography involves the measuring and mapping surface skin temperature through direct contact (via application of liquid crystal plates to a part of the body) or at a distance (utilizing a highly-sensitive medical infrared camera and sophisticated computer interface). Thermography can be used in conjunction with thermostimulation which applies thermal stress on the skin to be examined.

Other methods of providing an image include the use of multiphoton fluorescence microscopy or multiphoton excitation microscopy that use more than one photon excitation to illuminate endogenous fluorophores in skin tissues, which emits a fluorescence signal to be captured by a detector. Additionally, optical coherence tomography (OCT) may be used and this device utilizes reflected light to produce cross-sectional subcutaneous images of tissue at a resolution equivalent to a low-power microscope. Confocal scanning laser microscopy (CSLM) works by first projecting a low-power laser beam through a lens on a specific point on the skin, and then detecting the light reflected from the focal point through a confocal pinhole filter. The reflected light is transformed into an electrical signal, which is recorded as an image by a computer.

Photodynamic diagnosis includes the use of topical agents that stimulate the production of endogenous photosensitizers that produce a photodynamic effect when exposed to light of certain wavelengths and energy. For example, UV is absorbed by melanin. The theory behind this experimental technique is that illumination by ultraviolet light could reveal irregular pigment distribution, and therefore could be useful in defining the borders of melanoma.

The features extracted from the image are then used to classify the image wherein the classification step is comprised of characterizing the tissue based on features such as shape, color, size, or quality of the tissue, to name a few, and the characterization of a tissue is compared to the characterization of a reference tissue and the tissue is classified based on the comparison.

Figure 6:
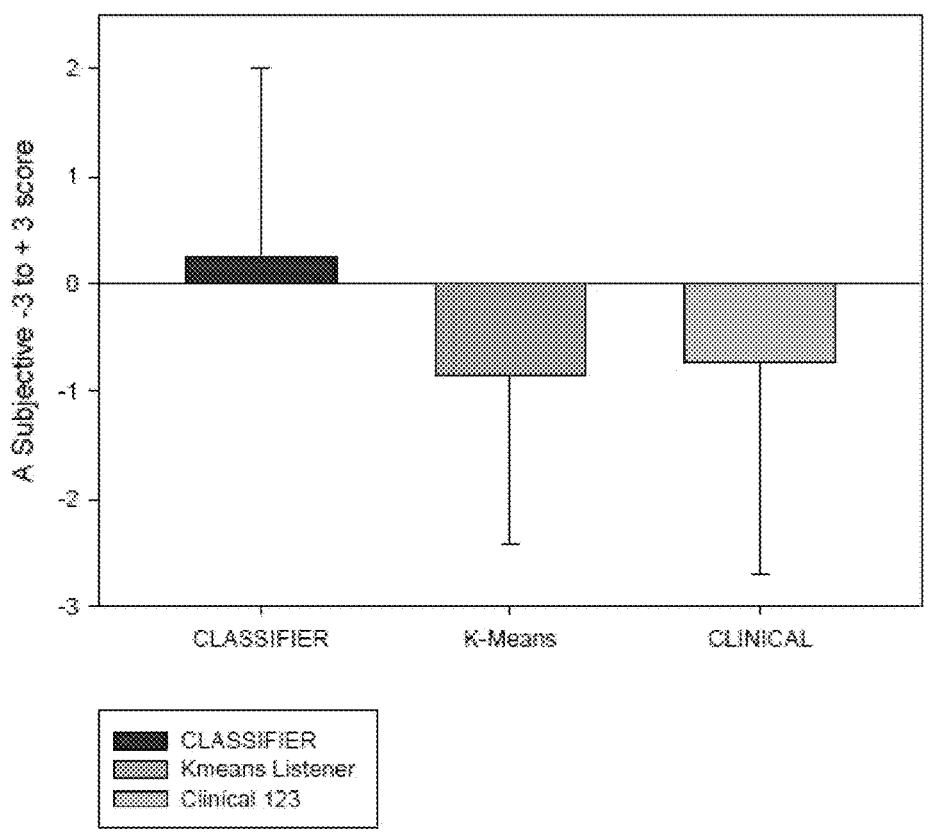
FIG. 6A shows a comparison of diagnostic accuracy between a deep learning classifier and a K-Means audio output as defined by pathology reports of 254 malignant lesions and 290 benign lesions. The K-Means sensitivity is 97% as compared to 83% by the classifier. In other words, the standard deep learning classifier missed 14% of malignancies. The K-Means Sonification amounts a negative predictive value of 95%, as compared to 84% for the deep learning classifier, i.e. a threefold increase in misdiagnosis of melanoma by an ubiquitous classifier deep learning visual technique.
FIG. 6B demonstrates a comparison between the Classifier, Clinical decision and Audio decisions which were compared on a scale from −3 (severe malignancy) to +3 (fully benign).

Embodiments of present invention can employ computer aided classification systems (sometimes termed "machine learning," or "deep learning"). There are a plethora of pattern recognition algorithms to employ to biometrically model and classify different tissue types. Those skilled in the art will recognize that many such classifications systems could be used in the present invention, including but not limited to Linear Discriminant Analysis (LDA), Kernel Discriminant Analysis (KDA), Neighborhood Preserving Embedding (NPE), Orthogonal Linear Graph Embedding (OLGE), Unsupervised Discriminant Projection (UDP), Marginal Fisher Analysis (MFA), Locality Preserving Projection (LPP), Local Fisher Discriminant Analysis (LFDA), Convolutional Neural Network (CNN), Support Vector Machine (SVD) and Kernel Correlation Feature Analysis (KCFA A preferred classification system is the CNN system that is used in order to automatically extract local feature. Some examples of a CNN system includes Lenets, Alexnet, Overfeat, VGG, RESNET, Googlenet and Inception (V2, V3, V4), ENET and Xception. CNN consists of many layers, each layer plays a feature extraction role and performs different operators such as convolutions, subsampling, pooling, full connection, etc. Similar to other neural network, CNN is trained by backpropagation. Based on performance, online error backpropagation is used in general. The learning process is an iterative procedure where the weights are updated by a small step in the opposite direction of the steepest gradient. The present invention has found that the use of sonification, i.e. of deriving audio data, in order to convey information, set up on a processed image employs variable tone input, melodic alarms and changes of sound patterns which meaningfully increase the spectrum of diagnosis. Specifically, transduction of patterns of visual information from a pattern analysis of a skin lesion into diagnostic sounds results in a much higher resolution rate and precision of diagnosis (FIG. 6). Thus the use of an audio signal corrects the human inability to distinguish between a myriad of two and three dimensional visual cues, which by themselves possess no specificity. On the contrary, pattern signal analysis using classification of data methods and a final integration of data into sound signals by an algorithm using pitch, amplitude, timbre, spatialization and temporal patterns confers a diagnostic advantage. The practitioner reacts to a divergence from a learned sound pattern and baseline, instead of reacting to each individual lesion. The final results are audio signals which can be easily assessed in order to recommend the proper medical procedure.

Parameter mapping sonification involves the association of information with auditory parameters for the purpose of data display. Since sound is inherently multidimensional, is particularly well suited for displaying multivariate data. Data exploration is often thought of as the most 'scientific' of sonifications and usually makes use of a type of sonification called parameter based sonification. For example, sonification approaches can be used to interpret and sonify the weighted activations of nodes in a machine learning system (computer aided classification system), including "Raw" weights sonification, Concept Mapping sonification and K-Means sonification.

K-Means is an unsupervised learning algorithm that classifies a given data set into certain number of clusters. The data is preferably gained from the classification systems discussed above, such as the CNN system. The main idea is to define k centroids, one for each cluster. Initially the algorithm preferably places the centroids far away as possible from each other. The next step is to take each point belonging to a given data set and associate it to the nearest centroid. Each point belonging to a given data set is associated to the nearest centroid. When no point is pending, the first step is completed and an early grouping is done. Again re-calculate k new centroids as centers of the clusters (resulting from the previous step). Repeat the process until centroids do not move any more. In the successive loops, the k centroids change their location step by step. In the present invention, each image has different features due to the type of skin cancer and such different features are used for classification. Texture is an important aspect of the image including brightness, color, slop and size. Such features are useful from the dataset of the image and can be used in the classification. In the present invention, it has been found that the number of centroids relating to the features of the visual skin image can range from about 8 to about 14 centroids, and more preferably from about 9 to 12. Thus an image filled with different points of data can be extracted and classified with a subsequent connection to an audio sound, generating various amplitudes, decays and frequencies of the sound.

Importantly, the audio sound includes different pitches, loudness, durations, timbres, and other sound attributes to make the malignant lesions sound comparatively more loud, sharp, or urgent than benign lesions. This difference in sound attributes allows an experienced listener to learn to differentiate the sound of different classes of lesions. Notably, using the sound attributes is diagnostically more powerful because audio output based on K-means provides a severity to a data point which utilizes the audio data collection of the brain which is more sensitive as compared to the visual examination. Specifically using an audio signal based on the K-means data can denote a severe malignant sound and the clinician may excise more margin and provide for a faster follow up based on this message.

The above extraction of data from the Classifier may be a standalone or combined with additional methodologies of sound extraction in order to represent it as sound, as exemplified but not restricted to: Raw weights analysis, i.e. defining an activated point in a processed classifier image as either benign or malign, assigning it a specific weight, and sorting by magnitude the sum of all in order to derive sequential sounds or/and by concept mapping data analysis, i.e. determining an infinite number of parameters, starting with, such as benignness, malignancy, color, as a linear or non-linear function of the distance and polarity of a given image from the benign/malignant/color decision boundary in a complex dimensional space represented by the classifier input, attributing a virtual weight to each, with or without multiplying each parameter by its confidence, average, root mean square, etc. and generating amplitudes, decays, and frequencies of the calculated sum of these activations.

The new device may be operational either as a stand-alone apparatus or as an added interface to an existing apparatus used for gaining visual data. It is the object of the present invention to acquire visual data, analyze it by pattern recognition rules of dermoscopy and transform it by parameter mapping sonification into a simple medical device (FIG. 1). The present invention provides for an effective diagnostic method and system that bypasses parts of the visual brain in the decision making process.

For exemplifying purposes, the device is described herein as being specifically designed for melanoma diagnosis. Nevertheless, it will be immediately obvious to persons skilled in the art that additional applications are possible, in particular diagnosis of cancerous skin diseases such as dysplastic nevus, actinic keratosis, basal and squamous cell carcinoma, or the use for definition of skin properties such as skin microstructure and wrinkles, which are another object of the invention, or to diagnose skin disease, alike identifying the existence of onychomycosis.

Figure 2:
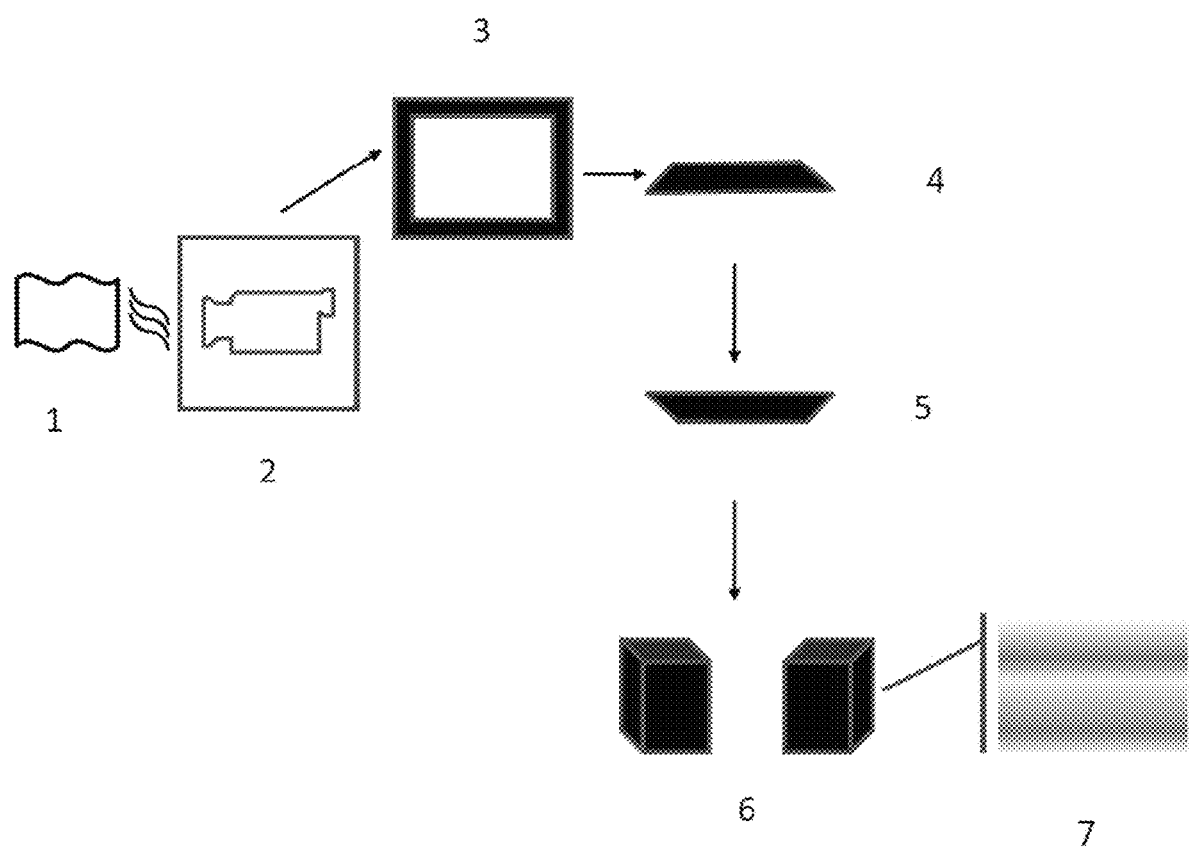
FIG. 2 shows a flow chart illustrating one embodiment of diagnosing a skin lesion, transducing electromagnetic waves into a visual input to be completed by pattern analysis and data to sound sonification.

Embodiments of the present invention are directed to application of pattern analysis recognition based, but not limited to, dermoscopy principles and sonification of the results. In one embodiment a standalone device acquires visual data from a skin lesion by an optical or mechanical method (FIG. 2), included but not limited to identifying a skin lesion (1), capturing by a sensor of refracted electromagnetic waves such as UVA, visible spectrum or infrared wavelenghts or molecular vibrations (2), further obtaining optical raw data on a dermoscopic device or computer screen (3), processing visual data by deep learning on site and applying a dermoscopic pattern analysis to the acquired image (4), transducing the data to an audio signal by Concept Mapping assigning different pitch, loudness, timbre, spatialization and temporal patterns to each visual pattern (5), to be communicated through an algorithm to the practitioner by an audio system (6), with or without an optional additional screen for visualization of audio data (7).

In another embodiment the present device acts as an interface between any existing apparatus which acquires visual image or images of a skin structure, in order to perform dermoscopic pattern analysis. Digital data is further to be assessed into a second processing unit which transforms processed visual data into audio signals, i.e. a parameter mapping sonification, taking advantage of basic sound recognition based on pitch, loudness, timbre, spatialization and temporal patterns of sound.

Figure 3:
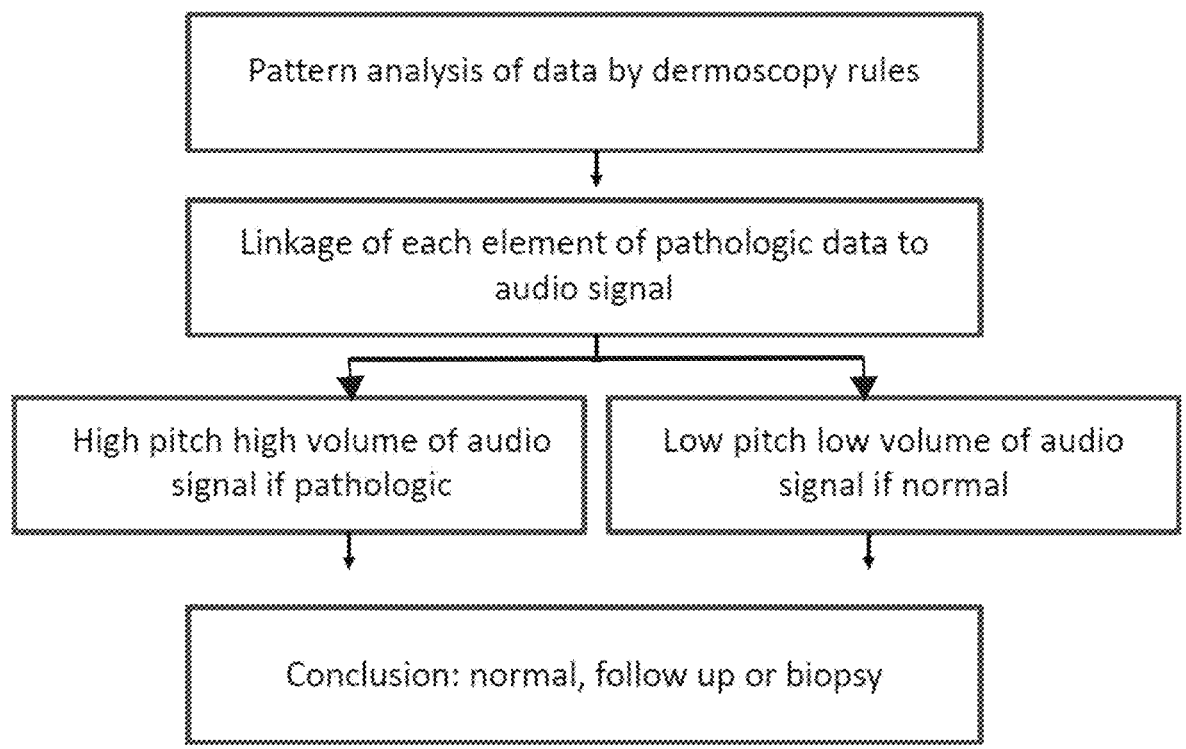
FIG. 3 shows a functional block diagram of one embodiment which leads to acoustical excise or do not excise diagnosis.

The present invention device is different from available methods and systems which use only digital or non-digital visual data and attempts to converge information at the end of a visual diagnostic stage in order to facilitate the diagnosis. In sharp contrast, the phonodermoscopy device of the present invention uses a system and method of creating a detailed mapping of digital data and diverging input during and at the end of visual dermoscopic pattern analysis stage. Data is further converted from a processed final feature map which was applied a dermoscopic features input by parameter mapping sonification of data, such as unsupervised learning K-Means Sonification input, which is converged into audio data at decisional points (FIG. 3). The phonodermoscopy device of the present invention informs of a constant basic ground noise which is specific to each individual lesion and diagnoses deviation from the normal baseline.

The main components of the system are: 1. a unit capturing electromagnetic waves from a skin lesion 2. a direct input optical data visual screen, 3. a visual data processing unit to a final feature map, 4.a dermoscopic pattern transduction process unit, local or on cloud 5. a visual to audio transducer unit and 6. a headphone/speaker unit. The clinician moves the diagnostic apparatus from lesion to lesion, obtaining the audio signal, alike a stethoscope.

Figure 4:
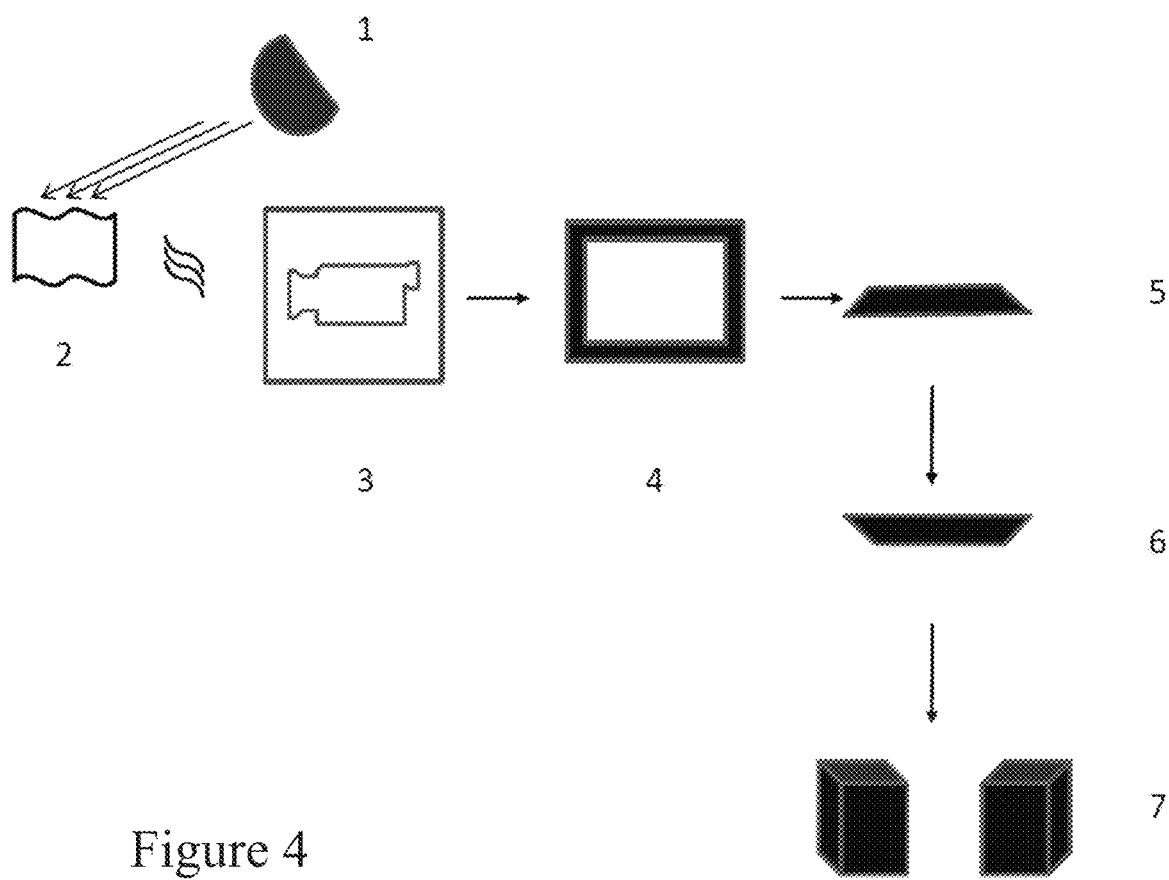
FIG. 4 shows a flow chart illustrating an embodiment of electromagnetic waves projection on a skin lesion and its further processing by data acquisition, data processing, and final sonification.

In some embodiments (FIG. 4), electromagnetic waves at various intensities, spectra and angles (1) are projected on the skin lesion (2) and image is captured by a dermoscopic device (3), processing visual data by deep learning on cloud and applying a dermoscopic pattern analysis to the feature map (4), transducing the data to an audio signal by K-Means Sonification and assigning different pitch, loudness, timbre, spatialization and temporal patterns to each visual pattern in order to provide a novel human-interpretable output to support clinical decision-making (5), to be communicated to a distant practitioner by an audio system (6), with or without an optional additional screen for visualization of audio data (7).

In yet other embodiments, the computer device analyzes skin photos and images derived passively from the skin lesion. In some embodiments, multidimensional images are obtained using multi spectrometry to be further processed for dermoscopy, classification through machine learning and sonification.

In one embodiment, the system stores the digital data and analyzes it by a dermoscopic pattern analysis, assigning various digital values to each pattern and area. Each nevus is given a full range of dermoscopic grading, by digital data and or color output, taking advantage of the next step of visual to audio transduction. The computerized software uses a normal nevus pattern as a baseline, assigning it values in order to be used as a control and future background noise, e.g. referring to in one embodiment by at least 6 colors and at least 19 basic patterns of dermoscopy. Visual nevus dermoscopic structures are converted into numerical values, assigning each skin structure a definite figure. Diverse structural areas in a nevus might be referred to by the same algorithm.

A full digital data map representing each skin lesion is developed to be further converted to audio signals. For example, by the use of conversion to audio, normal nevi are given a low pitch, low amplitude and basic timbre notification as compared to abnormal skin structures alike melanoma, which degree of irregularity generate a high pitch, high amplitude, high timbre and irregular pattern. Dysplastic nevi are assigned with intermediate degrees of amplitude and amplitude. The melanoma risk score derived from visual to audio conversation is divided into a highly sensitive arbitrary scale, and the practitioner is alerted by the change from baseline audio noise. Additional special pattern analysis melanoma identifiable risk factors allocated with a high amplitude. Specifically and contrary to existent systems, the diagnosis is not related to the status of the skin lesion in the past, and the diagnosis is absolute. Specifically and contrary to existent systems and systems which quantify melanoma risk in a limited scale, e.g. in a go no go indication to biopsy, the phonodermoscopy device of the present invention may quantify data into a much higher sensitivity scale. For example, in one embodiment a timbre of 1-61 keys, alike an organ, is employed. Another embodiment may use a short range of 1-25 keys, alike a synthesizer keyboard, which together with amplitude variation should indicate the degree of risk. Yet another embodiment may use a 3 octave sound scale, and an artisan in the art grasps the wide field of sound simulation, starting with use of any musical instrument or combination thereof.

The audio output of the system may be used especially but not limited to a stereo output. Head phones, multi speaker, iphone, etc. and any means might be used for audifing the data. A usual frequency range of 15 Hz-25 KHz, preferably between 20 Hz and 20 KHz for auditory perception.

In some embodiments, in order to facilitate assessment, the final audio data might be further converted to visual data on screen, expressed as a wave with amplitude and time, a bar graph showing intensity of signal or an algorithm which turns into quiet, e.g., blue colors or vivid red the audio data. For example, a dysplastic nevus, a lower level of pathologic entropy, may be assigned pink and orange colors.

Further, when using a digital device for capturing the image, such as a smartphone, in order to stabilize the procedure of image acquisition of the dermoscope image the image may be captured as well by voice recognition technology as an alternative to pressing all the buttons for acquiring the image, including the start and play button. The results and output may also be delivered by voice recognition technology.

Such audio data qualifies a primary care physician who uses the system in the diagnosis of melanomas. All data may be further recorded by the computer as visual and audio data, enclosed to the patient file. Such data may be further processed and transmitted as a medical record.

The phonodermoscopy system of the present invention is not limited to melanoma diagnosis, but to skin carcinoma and dysplastic nevus and actinic keratosis diagnosis, as well as to general skin wrinkle assessment, skin damages by sun, vascularization extent, skin pigmentation, nail fungi identification, etc., all those to be represented by specific sound patterns. In one embodiment a piano sound may be assigned to melanocytic nevi lesion, while a trumpet sound assigned to carcinoma. In other embodiments, the systems of the present invention are inverted, or instruments changed by the user. In another embodiment, skin wrinkles audification may be presented as low pitch low amplitude for minor wrinkles and as high amplitude and noise for numerous wrinkles. In another embodiment, onychomycosis induced by a candida is allocated with a high amplitude and rate as opposed to onychomycosis caused by trichophyton, which is endowed with a low amplitude, thereby determining the etiological source.

Further, the high sensitivity of phonodermoscopy method and system of the present invention can be used as a dynamic tool for skin quality assessment, for wrinkles, blood vessels and pigmentation.

Figure 5:
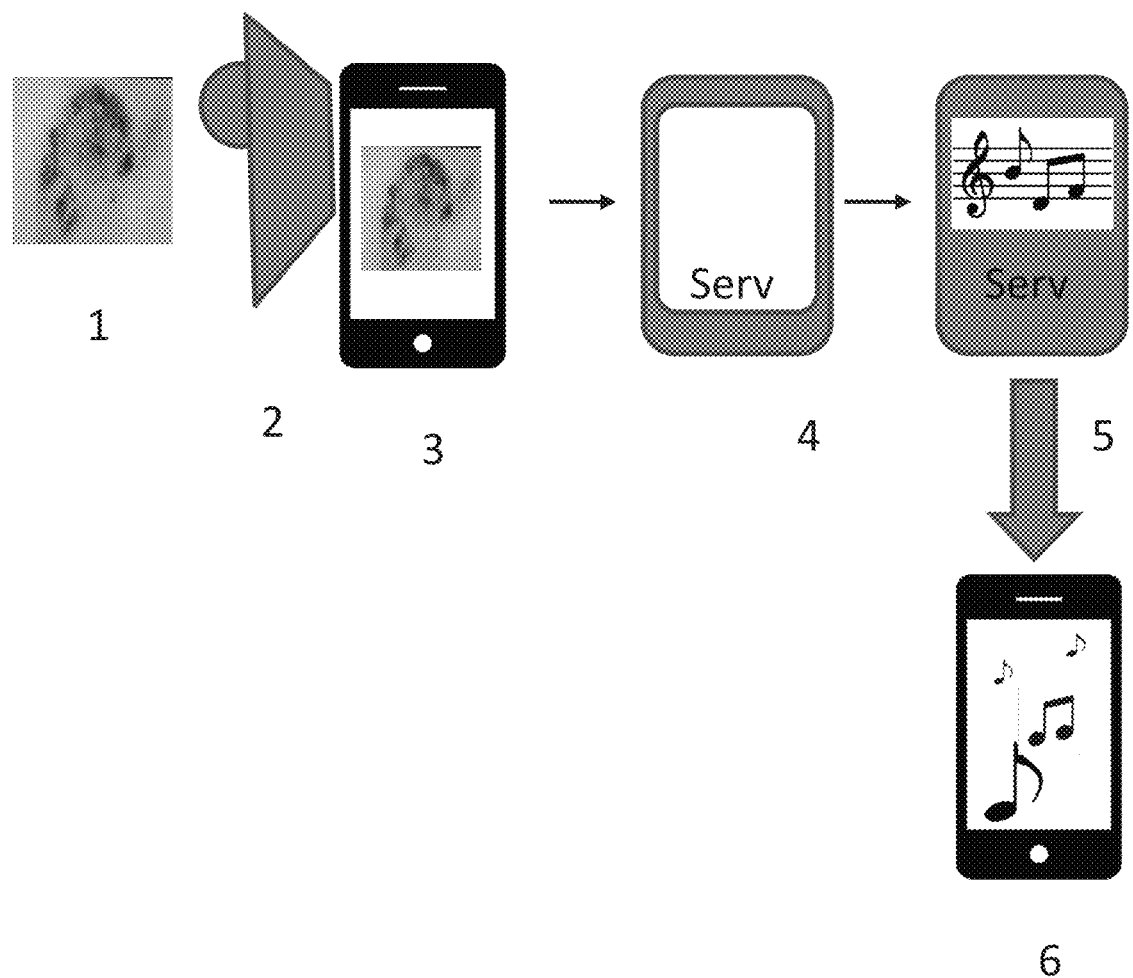
FIG. 5 shows a schematic of an embodiment using a smart phone as an interface to move a visual image for conversion to an audio signal.

FIG. 5 shows a schematic for the steps used by a dermatologist in diagnosing skin tissue and providing an accurate diagnosis using a smart phone app and a sonification approach. A dermoscopic image (2) of a suspect lesion (1) is acquired and transferred through a smartphone (3) to a server that has a program to evaluate the image using pattern signal analysis (4) and then data is further processed using classification of data methods with a final integration of data into sound signals by using parameter mapping sonification (5). The process involves the association of data of the image with auditory parameters including pitch, amplitude, timbre, spatialization and temporal patterns. The audio signal is sent back to the dermatologist for a final diagnosis (6).

FIG. 6 estimates positive and negative predictive values for unsupervised K-Means sonoscopy and a supervised deep learning classifier which employed the supervised Inception V2 network architecture. A total of 570 biopsies were evaluated by Sonoscopy and Classifier Deep Learning, 290 benign and 254 malignant. The sensitivity to melanoma detection of the sonoscopy methodology was 97% as compared to a 84% value of the classifier. The K-Means Sonoscopy amounts a positive and negative predictive values of 61% and 95%, respectively as compared to a positive and negative predictive values of 79% and 84% for the deep learning classifier. Negative predictive value, the probability that subjects with a truly negative screening test are not diagnosed as melanoma is 95% for Phonodermoscopy and only 84% for visual only classifier deep learning, i.e. classifier misses diagnosis in 16% of subjects, as compared to 5% of K-Means sonoscopy, a X3 fold increase. A 11% misdiagnosis of melanoma, a deadly disease, by usual deep learning visual techniques, is highly significant and underlies the higher sensitivity of the present Phonodermoscopy invention. A 11% difference between methodologies is a heavy price to be paid by patients with this lethal disease. On the contrary, a 18% difference in positive predictive value, the probability that subjects with a positive screening test truly have the disease, represents a small margin of safety to be paid for an increase in sensitivity. Correspondingly, the Pearson Product moment between the two methodologies was 0.74, a relatively weak figure.

FIG. 6B demonstrates a comparison between the Classifier, Clinical decision and Audio decisions which were compared on a scale from −3 (severe malignancy) to +3 (fully benign). A Kruskal-Wallis One Way Analysis of Variance on Ranks and All Pairwise Multiple Comparison Procedures (Dunn's Method) were employed in order to investigate the relationship between the three tested parameters. K means and Clinical decisions correlate and are significantly different from Classifier (p<0.05). K-means and Clinical decisions are similar, without reaching any statistical significance as shown below in Table 1.

TABLE 1

| Kruskal-Wallis One Way Analysis of Variance on Ranks All Pairwise Multiple Comparison Procedures (Dunn's Method) | | | |
|---|---|---|---|
| Comparison | Diff of Ranks | Q | P < 0.05 |
| Classifier vs Kmeans Listener | 279.858 | 11.040 | Yes |
| Classifier vs Clinical 123 | 257.422 | 8.834 | Yes |
| Clinical 123 vs Kmeans Listen | 22.436 | 0.768 | No |

Figure 7:
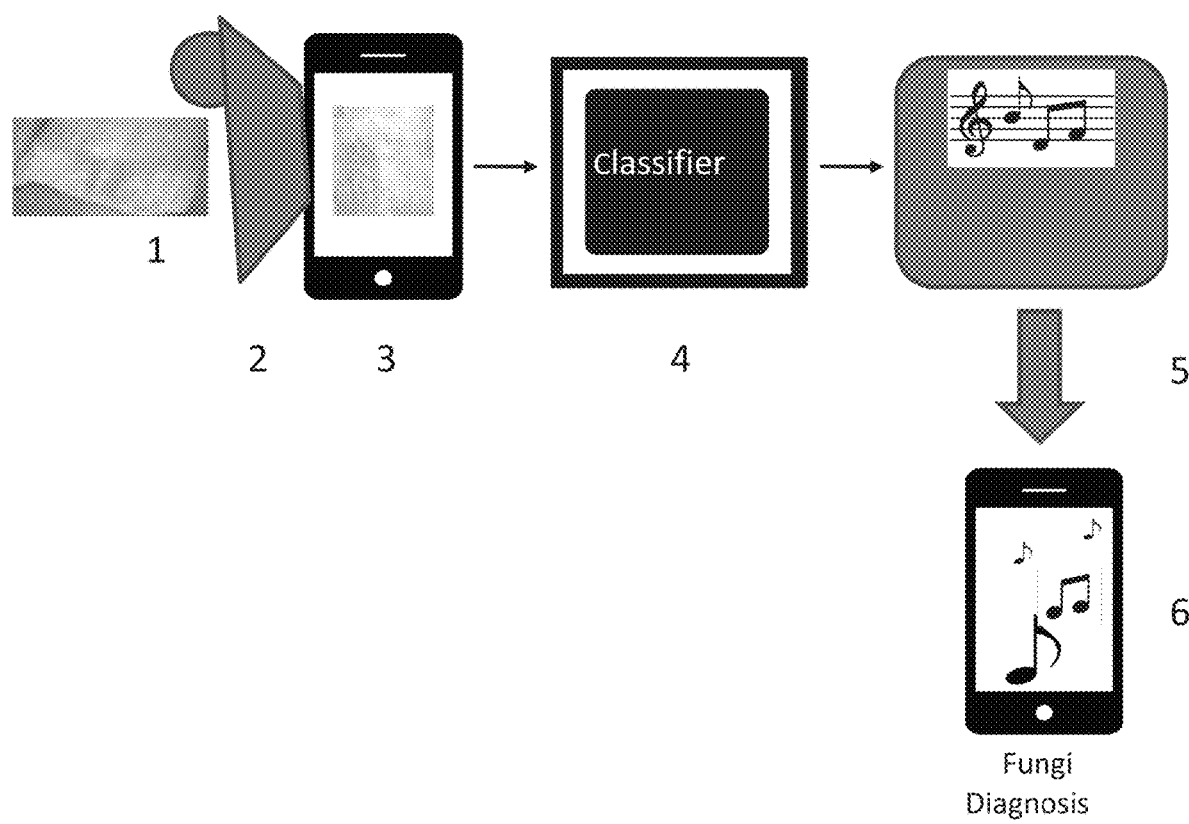
FIG. 7 shows a schematic of an embodiment using a smart phone as an interface to move a visual image for conversion to an audio signal and providing results for onychomycosis diagnostics.

FIG. 7 demonstrates additional use of the classifier-derived sonification technology for onychomycosis diagnostics. A nail infected by fungi manifests changes in shape, density, border and color (1), which can be captured by camera or dermoscopy technology (2 and 3), and classified in a database with assistance from a deep learning system (4), diagnosing the existence of onychomycosis and by a specific etiological pathogen, such as alike candida or trychophyton. Sonification of classifier data by a K-means sonification (5 and 6) will increase precision and establish the final diagnosis.

EXAMPLES

In the following examples the images were first analyzed by a convolutional neural network (CNN) classification system to provide to provide a pattern and image recognition output by using deep learning of different layers of features. Specifically, the inception V2 classification program was used for classification which is a computer aided program that performs image classification by looking for low level features, such as edges and curves, and then keeps building up to provide a series of convolutional layers. Photographic images of both malignant and benign tissue lesions were introduced into the classification system. The classifiers identified by the CNN system were then inputted into a clustering algorithm. In the tests, the inventor of the present invention used the K-Means clustering algorithm to segment the lesions.

As discussed above, K-Means clustering separates n object into k cluster wherein each object belongs to the cluster with the nearest mean. The objective of K-Means clustering is to minimize the total intra-cluster variance so that then objects are forced into a few clusters thus have a small number of "centroids." That is, the images in the classifier database are forced into a few clusters, with each cluster having a centroid. The number of clusters (k) is arbitrary, and is set by the person running the K-Means algorithm. In the present invention, the number of clusters (k=11) was chosen after using a machine learning process. The resulting clusters or centroids do not have any special meaning; this is just a mathematical way to force some grouping of the images based on their various features. These 11 centroids were then sorted according to their predictive power for classifying lesions as benign or malignant. The main point of this approach was to reduce the data coming from the classifier down to, in this case, 11 numbers.

The sonification aspect involved assigning a pitch to these 11 centroids, wherein the centroids that more consistently predict benign lesions were mapped to lower pitches; and centroids that more consistently predict malignant lesions mapped to higher pitches. Since there are only 11 centroids, there were only 11 pitches required; thus each is mapped onto a proper musical note (i.e., a key on the keyboard), without the need to subdivide the keys up into micro-notes. The notes are separated by musical fourths, again centered around middle C. In addition to the pitch arrangement, the malignant centroids became more salient by applying a saw wave frequency modulator whose frequency increases with increasing malignant predictive power.

Test images were processed by the machine learning system, which, in the above-discussed K-Means approach produced 11 numbers, which represent the distance from that image to each of the 11 centroids. These 11 distance measures were then used to adjust the loudness and duration of each of the 11 notes making up the sonification system. Notably, these 11 notes can be played in a number of ways. They can, for example, be played simultaneously in an 11-note chord. Or, they can be played sequentially in an arpeggio-like manner. Or, they can be played in two simultaneous arpeggios, "from the middle out". The pitches, loudness, durations, timbres, and other sound attributes can all be adjusted to make the malignant lesions sound comparatively more loud, sharp, or urgent than benign lesions. The overall effect of this K-Means sonification approach was that the sonification still conveys information about the image, and how it compared to clusters of known images that are already in the database. However, relatively little is done to weight how the sounds come out (though, as just described, some of that can be employed), so the sonification allows the listener to have a clear sense of the components of the sound. This should, in turn, allows the experienced listener to learn to differentiate the sound of different classes of lesions. That is, the listener should be able to learn the sound of a seborrheic keratosis, as distinct from the sound of some other type of lesion. This is more diagnostically powerful, in theory, than simply distinguishing "something that is malignant" from "something that is benign". The method and system of the present invention is more congruent with how experienced diagnosticians use visual information (i.e., visual inspection, or even just the images of lesions) because they can make a more fine-grained assessment than just malignant/benign, but instead can assign a category or type to the lesion, which is part of their overall clinical diagnosis.

Reviewing FIGS. 8 to 17 it is evident that the present invention provides not only a visual image, but also the results of the computer aided classification system with the subsequent use of the sonification approach provides an audio signal and a bar graph showing data that represents a visual image of the audio signal.

All examples compared the classifier output as a double blinded evaluation versus the K-Means Sonoscopy, which was annotated prior to the deep learning enhanced classifier results. Both Sonoscopy and Classifier estimations ranged on a scale from +3 (benign) to −3 (malign) and were finally compared to the biopsy results, the ground truth. Clinical recommendation was also included by expert dermatologist who was blinded from classifier and biopsy.

Example 1

Figure 8A:
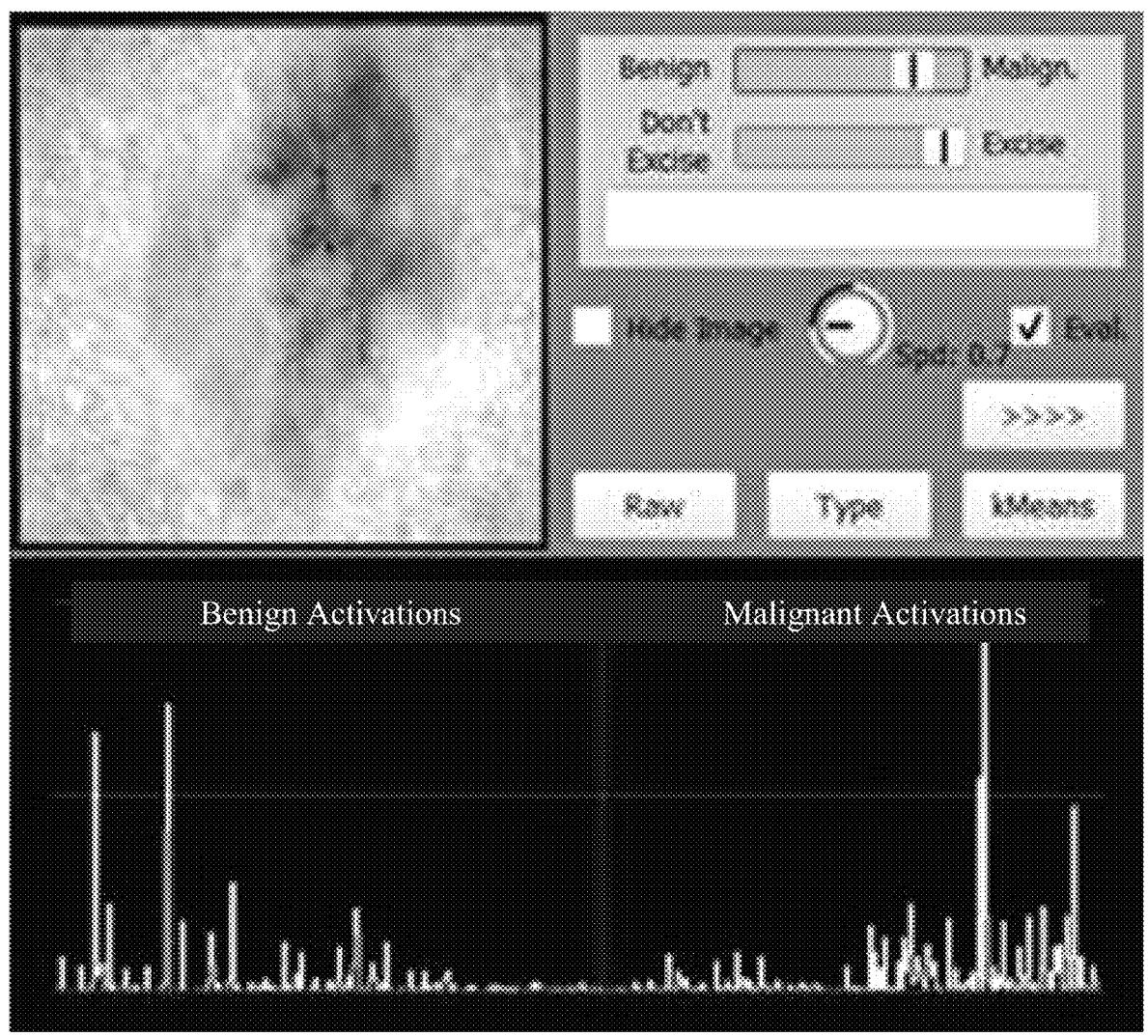
FIGS. 8A and B show image and audio indication (bar graph) of a malignant melanoma FIGS. 9A and B show image and audio indication (bar graph of activations) of a benign lesion.
Figure 8B:
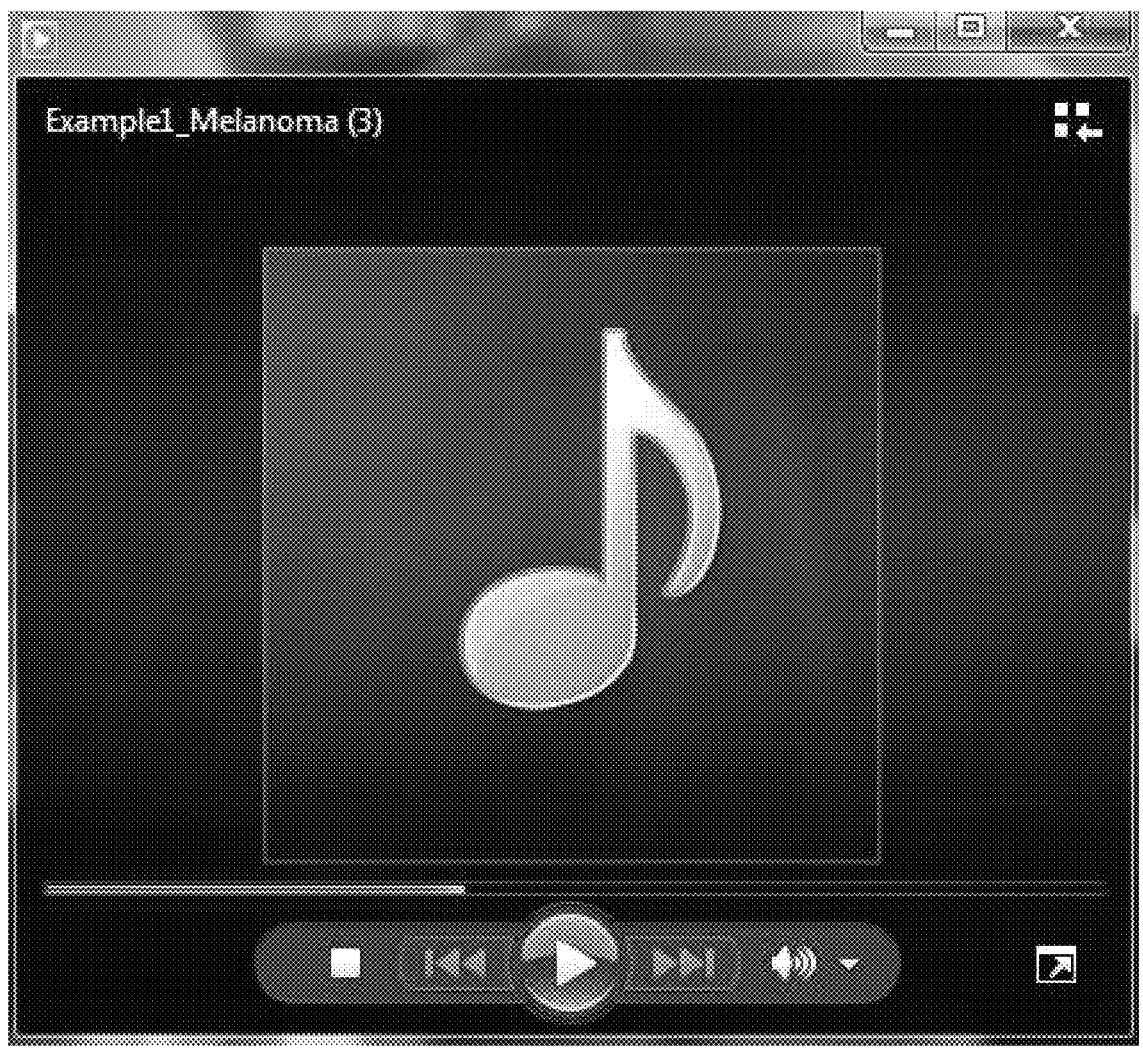

An example of Melanoma detected by K-Means Sonoscopy and Deep Learning Classifier. A higher sensitivity of Sonoscopy of −2 as compared to a Classifier degree of −1 is to be noted. The audio annotation indicates the higher amplitude of malignant activators on the right side, corresponding to a −2 degree. Reviewing FIG. 8A the top box depicts the audio output K-Means recommendation from a −3 (malign) to +3 scale (benign)(+3 +2 +1 0 −1 −2 −3). The second line shows the clinical diagnostic recommendation by expert dermatologist −3 (right) to +3 scale (left). The audio sound is depicted on bottom part, left side as "benign", right side as "malign". This example shows a clearcut Melanoma. Notably, K-Means sonification detected a more severe −2 need for biopsy. While the classifier agrees but only with a −1 degree. Notably the higher amplitude of malignant activators on the audio scale provides an audio indication of the melanoma. FIG. 8B provide an illustration of the opportunity for listening to audio relative to the malignant tumor.

Example 2

Figure 9A:
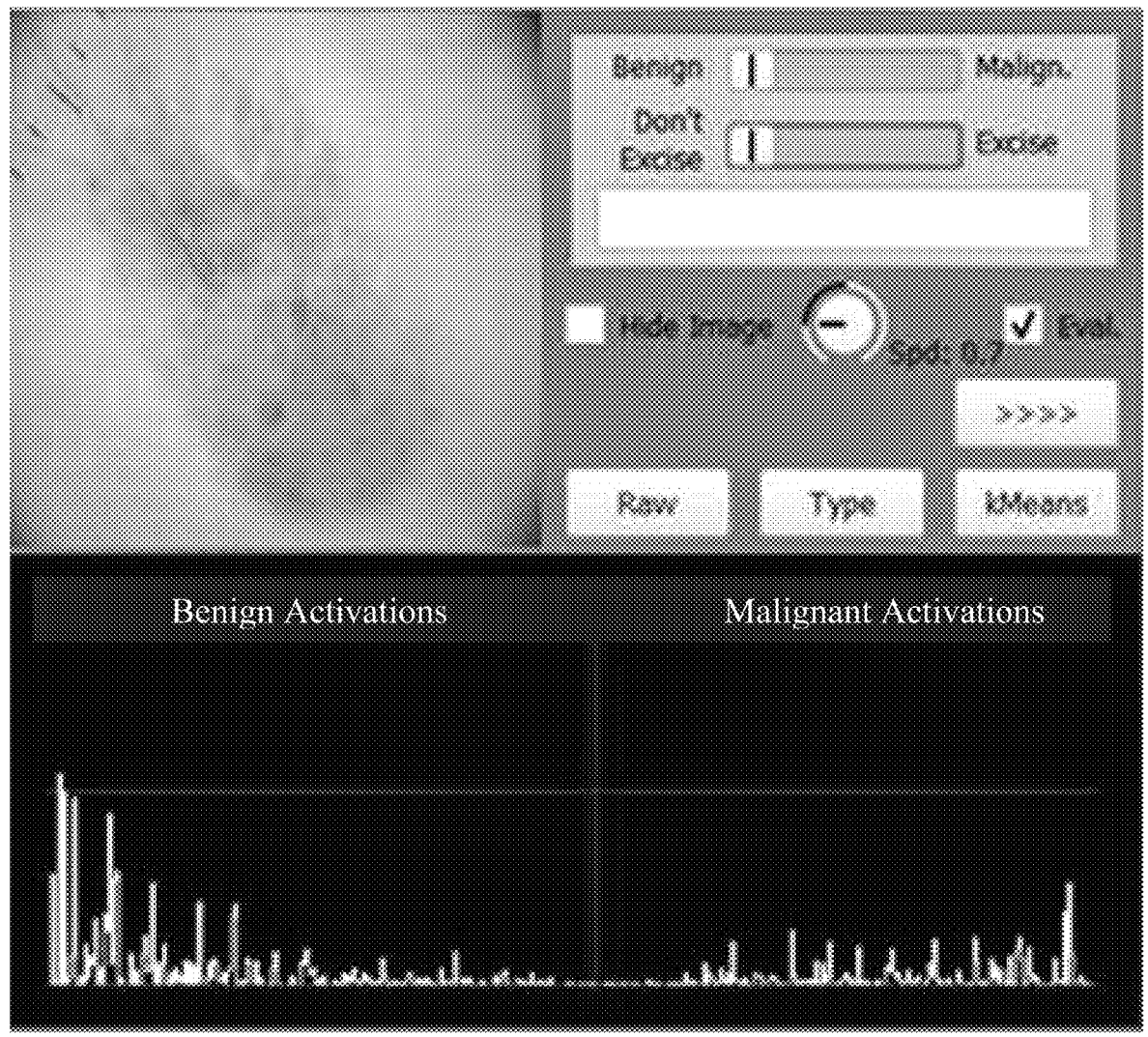
Figure 9B:
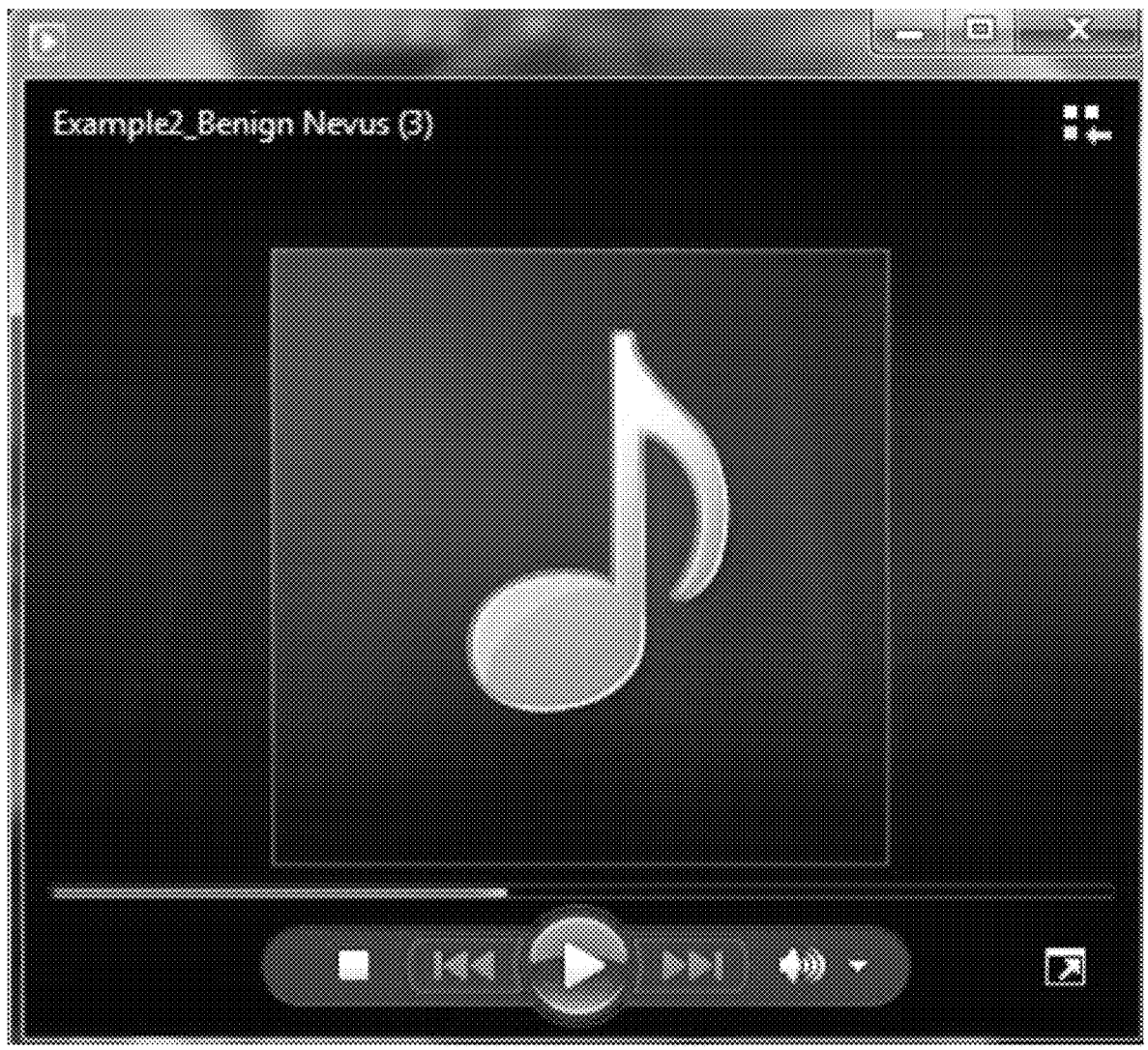

FIG. 9A shows a benign lesion by the pathological report. The K-Means Sonification approach delivered a +3 diagnosis and the classifier delivered a +2 score. There was a concordance between methodologies, although the sonification results was more categorical. The first line depicts the audio output K-Means recommendation from a −3 to +3 scale. The second line provides the clinical recommendation by expert dermatologist. Sound is depicted on bottom part, left side as "benign", right side as "malign". The results show a benign lesion of a +3 K-Means Sonification approach and the classifier delivers a +2 score. FIG. 9B provide an illustration of the opportunity for listening to audio relative to the benign lesion.

Example 3

Figure 10A:
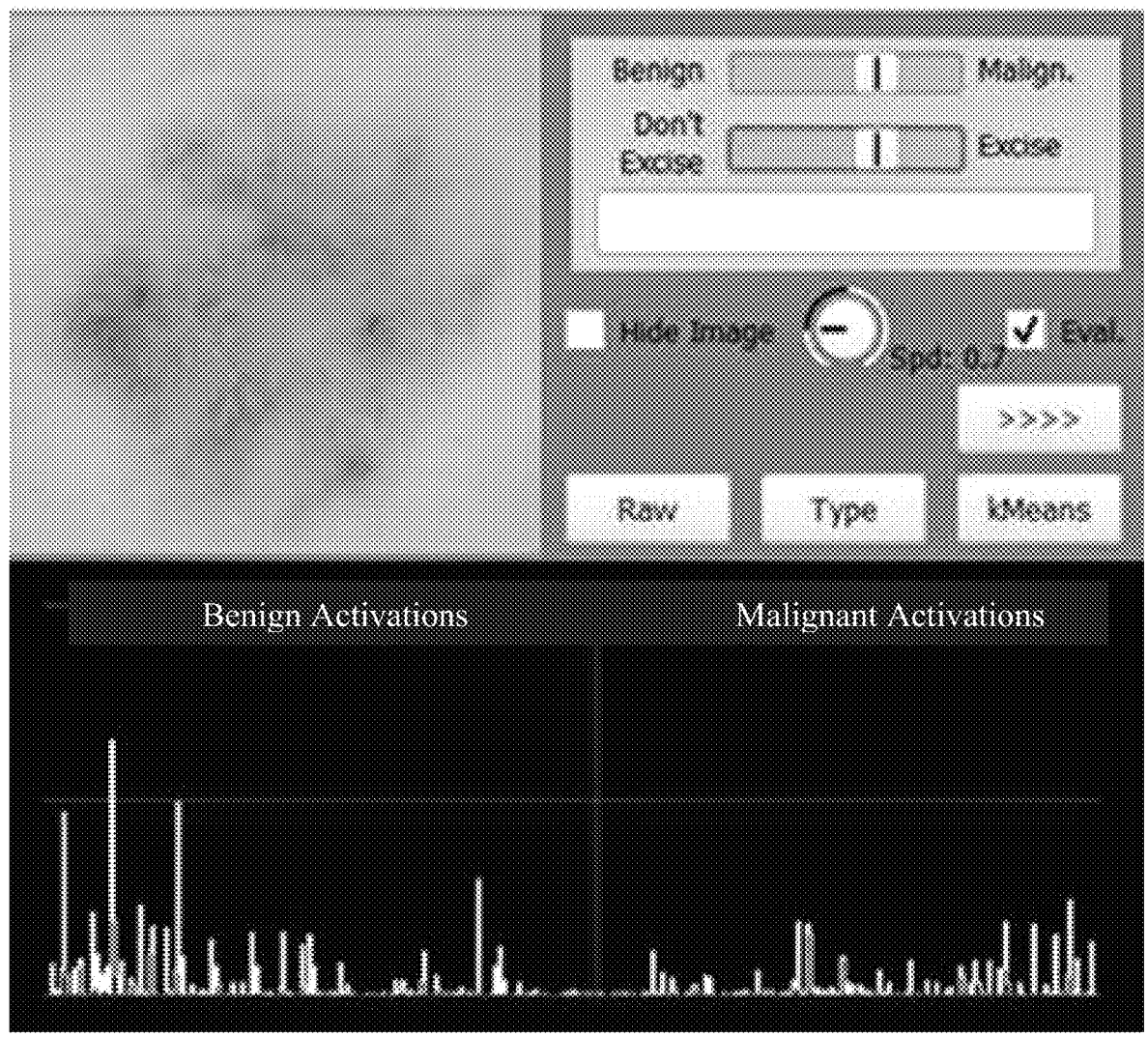
FIGS. 10A and B show image and audio indication (bar graph of activations) of a malignant lesion wherein the results of clinical evaluation and audio sonification differ from classifier.
Figure 10B:
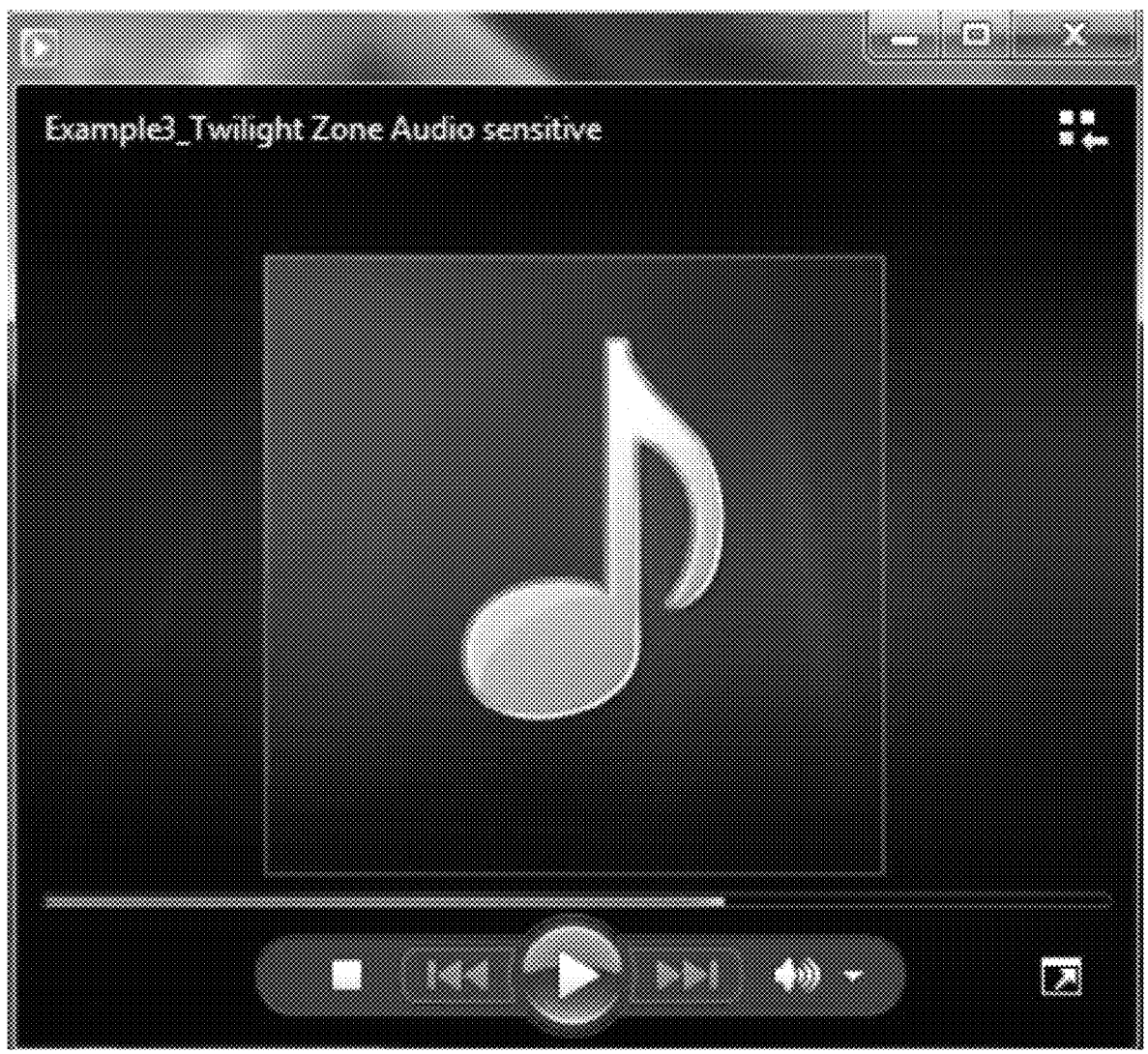

FIG. 10A shows a malignant lesion with a difficult diagnosis. Notably, it was identified by both clinical diagnosis and by sonification as malignant and that it should be excised. The classifier, however, reports a +0.4 score which trends to benign. Audio proves to be more sensitive and the pathological report endorses Sonification. Again the first line depicts the audio output K-Means recommendation from a −3 to +3 scale. The second line clinical recommendation by expert dermatologist. K-Means Sonification showed a value of (−1) and the clinical decision of (−1) wherein both recommended for excision. However, deep learning classifier, quantified a 0.4 score, i.e. a non excise diagnosis. Pathology was malignant and the sonification method contradicted the classifier. FIG. 10B provides an illustration of the opportunity for listening to audio relative to the malignant lesion.

Example 4

Figure 11:
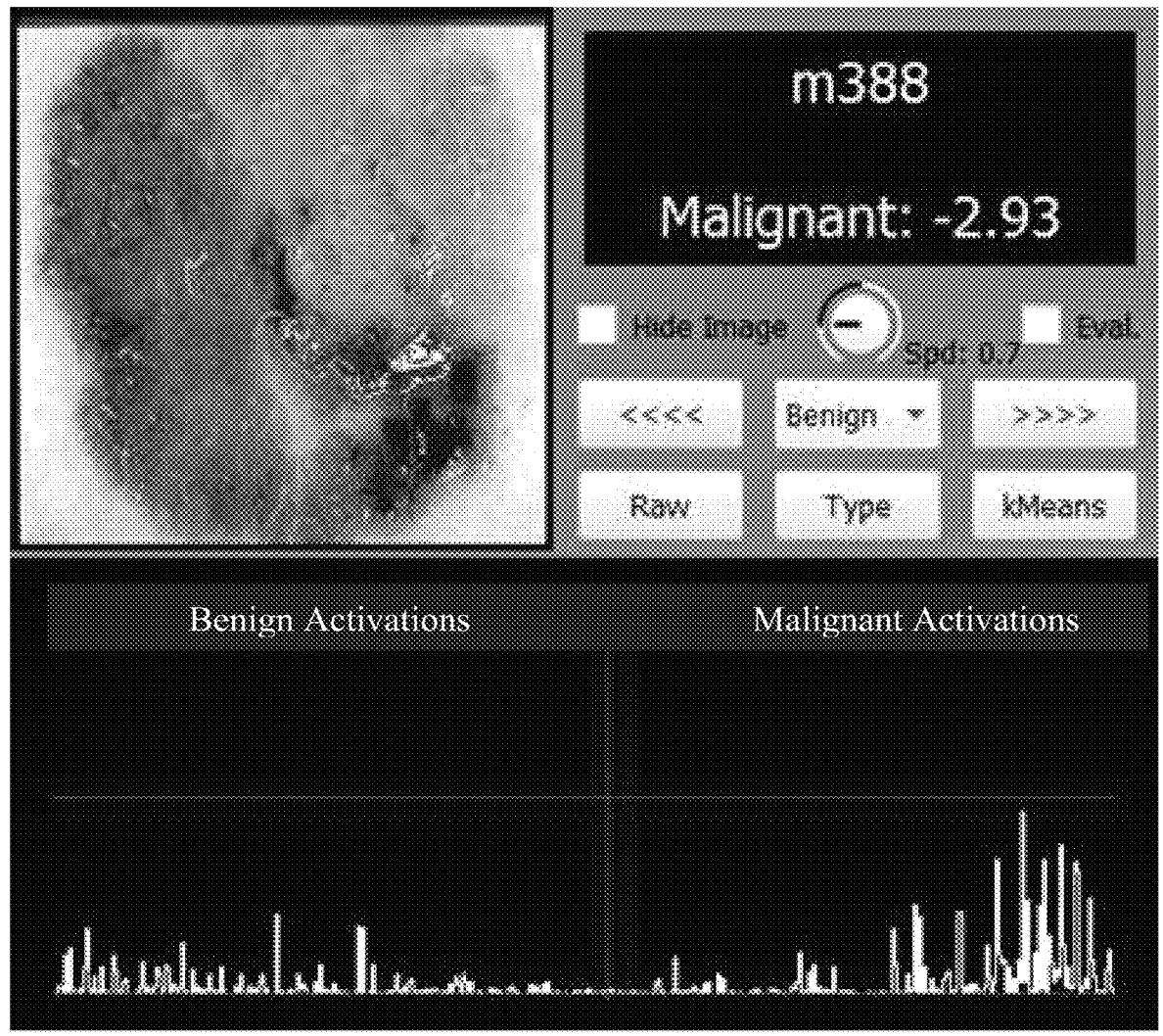
FIG. 11 shows image and audio indication (bar graph of activations) of a malignant melanoma.

FIG. 11 shows Malignancy depicted by K-Means Sonification and Deep Learning Classifier. First line depicts pathological diagnosis, m for malign and b for benign and the specific malign biopsy no, 388. Second line depicts the classifier deep learning recommendation from a −3 to +3 scale. K-Means Sonification output assessed and double blinded from classifier and biopsy results. Audio is depicted on bottom part, left side as "benign", right side as "malign". A malign nevus by all means, see a −2.93 score and malignant activators on sound scale, as well as amplitudes of sonification. Note an asymmetry of color and shape, peripheral pigmentation and black color.

Example 5

Figure 12:
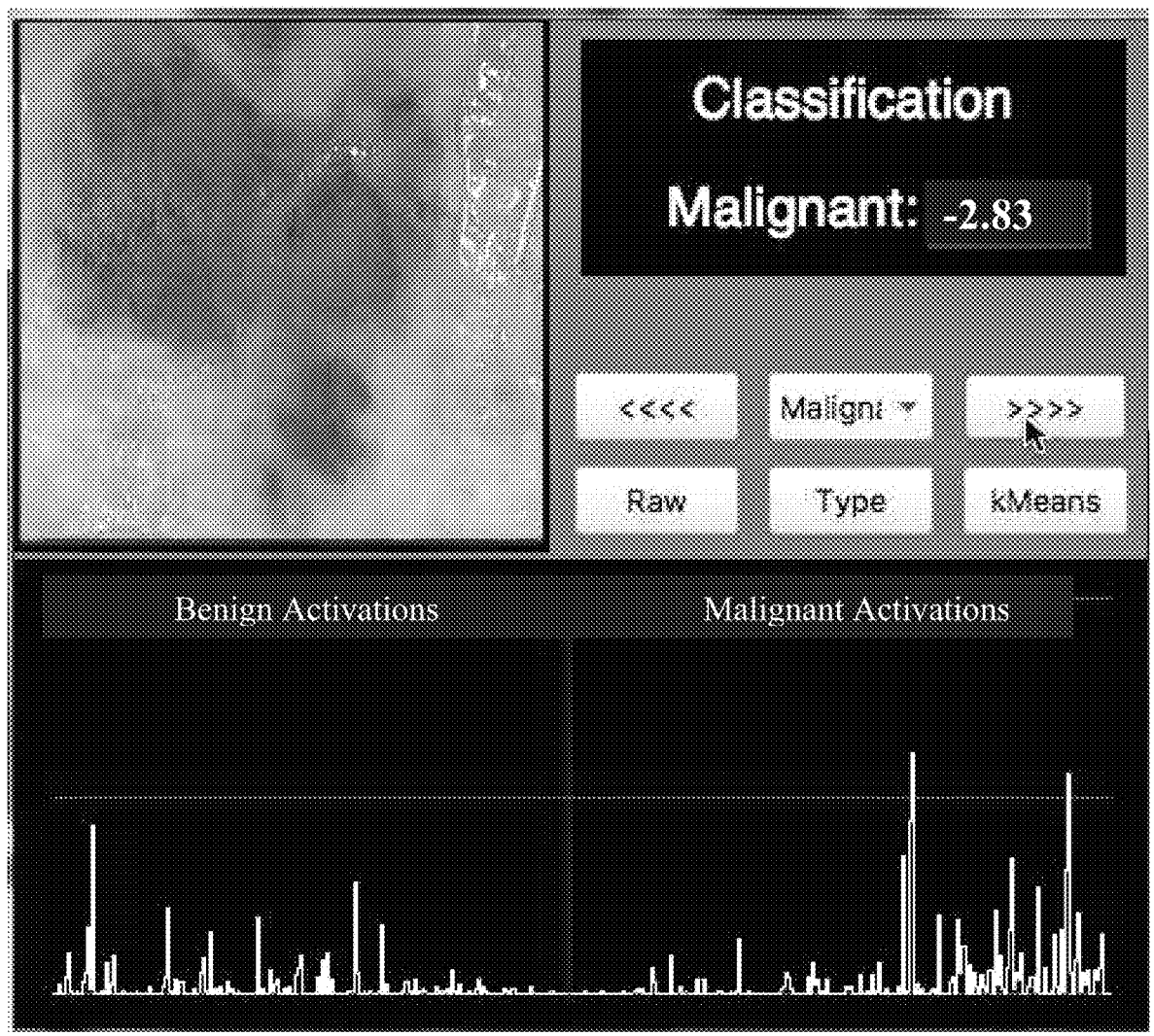
FIG. 12 shows image and audio indication (bar graph of activations) of a malignant melanoma

FIG. 12 shows malignancy depicted by K-Means Sonification and Deep Learning Classifier. Reviewing the bottom section of FIG. 12 shows higher pitch (amplitude) on the malignancy activation part of the scale. The classifier deep learning recommendation is from a −3 to +3 scale and shows a −2.83. This malignant melanoma was found by all methods including deep learning classifier −2.83, malignant activators and amplitudes of sonification. Note a blue white veil, as pathognomonic by dermoscopy.

Example 6

Figure 13:
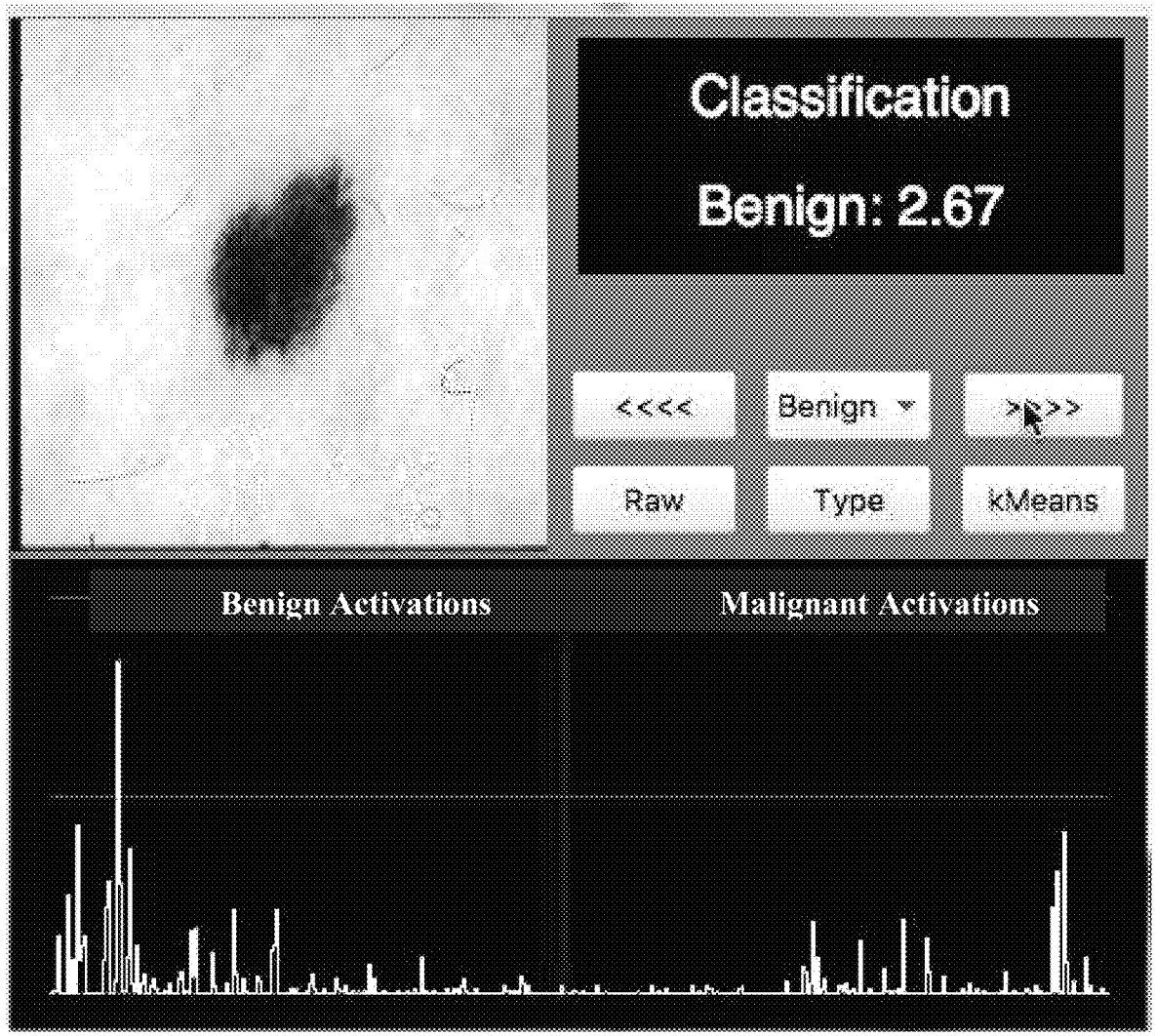
FIG. 13 shows image and audio indication (bar graph of activations) of a benign lesion.

FIG. 13 shows a benign nevus depicted by K-Means Sonification and Deep Learning Classifier. Higher pitch (amplitude) on the benign activation part of the scale. The classifier deep learning recommendation is from a −3 to +3 scale and shows a 2.67 benign. This benign nevus was found by all methods including deep learning classifier 2.67, malignant activators and amplitudes of sonification. Note a symmetry of color and shape.

Example 7

Figure 14:
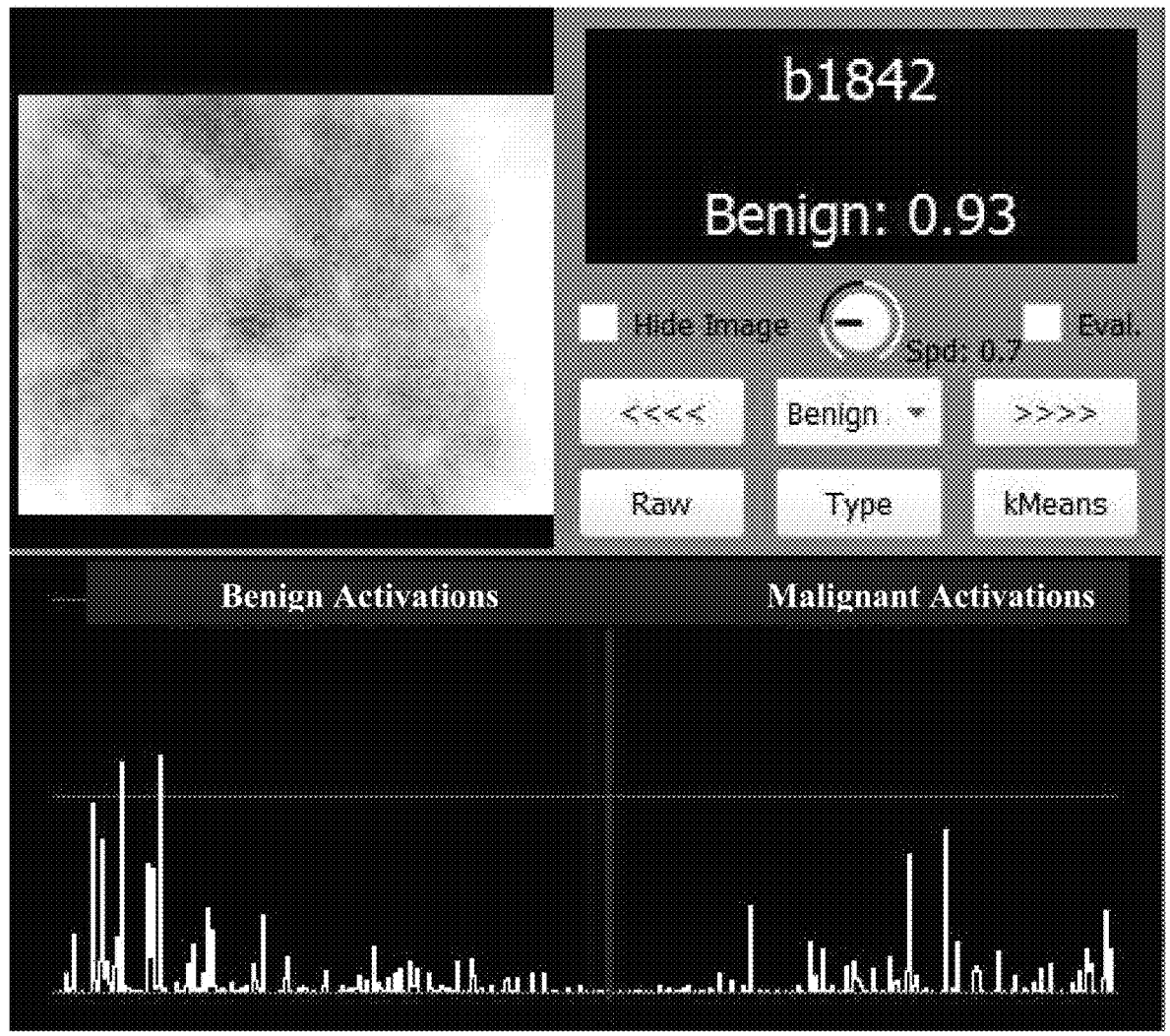
FIG. 14 shows image and audio indication (bar graph of activations) of a benign lesion.

FIG. 14 shows a benign nevus depicted by both K-Means Sonification and Deep Learning Classifier. Sound depicted on bottom part of the picture wherein the left side is denoted as "benign" and the right side as "malign." Notably there is higher pitch (amplitude) on the benign activation part of the scale. First line depicts pathological diagnosis, wherein b for benign and the sample biopsy. Second line depicts the classifier deep learning recommendation from a −3 to +3 scale with a value of 0.93. The K-Means Sonification was assessed double blinded from both classifier and biopsy results. All methods found the lesion to be benign. That being, a benign nevus, depicted by classifier and benign activators distribution and amplitude. Note a symmetry of color and shape.

Example 8

Figure 15:
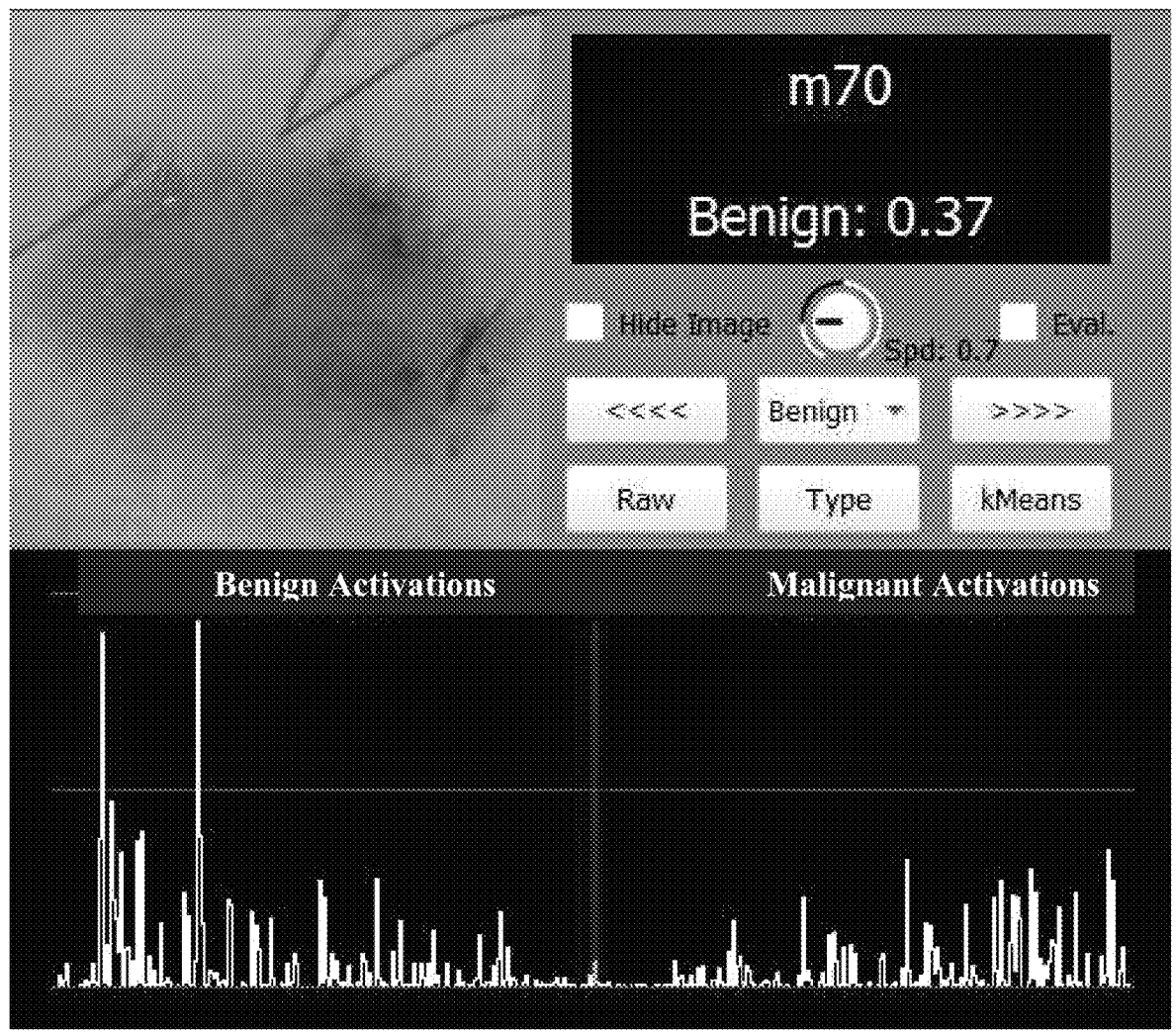
FIG. 15 shows image and audio indication (bar graph of activations) of a malignant lesion wherein the results of pathology and audio sonification differ from classifier result.
Figure 16:
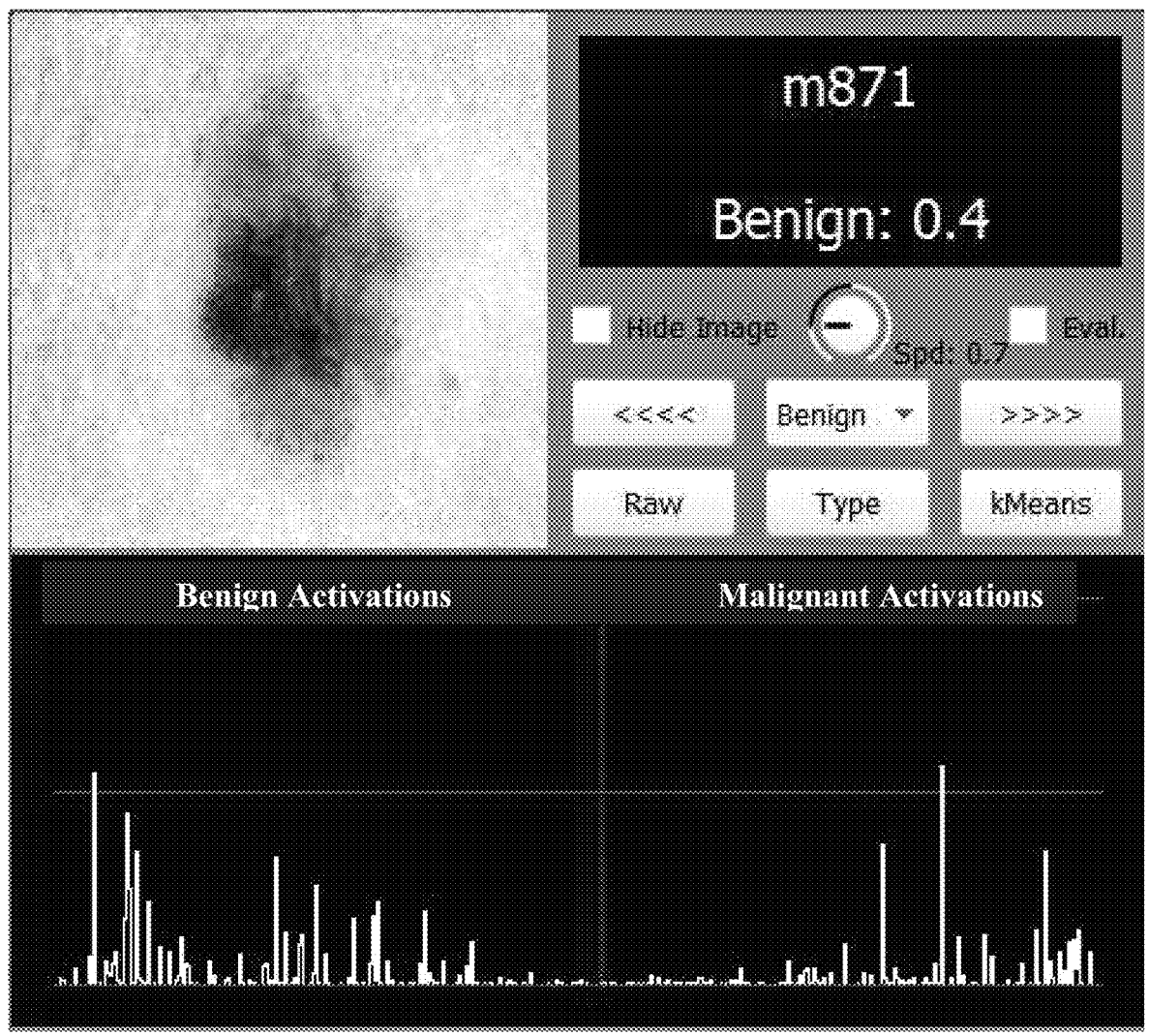
FIG. 16 shows image and audio indication (bar graph of activations) of a malignant lesion wherein the results of pathology and audio sonification differ from classifier result.

FIG. 15 shows the lack of constituency between the different methods, and specifically there is contradicting diagnosis between Sonification (−1) and Classifier (+0.37). Pathology agrees with sonification, rendering it as the more sensitive method. Importantly, by deep learning diagnosis it should not be excised, but clearly this is a mistake because the lesion is malignant. First line depicts pathological diagnosis, that being m for malign and the biopsy sample is No 70. The second line depicts the classifier deep learning recommendation from a −3 to +3 scale and provided a number of 0.37 which indicates benign and no excising. Again the K-Means Sonification was assessed double blinded from the classifier and biopsy results. There is a discrepancy between Sonifier (−1) and pathology (malign) to Classifier, a 0.37 score of do not excise. Note peripheral dots, a pathognomonic sign of dermoscopy.

Example 9

FIG. 16 again show contradicting diagnosis between Sonification (−1) and Classifier (+0.40). Pathology agrees with sonification, rendering it as the more sensitive method. By deep learning diagnosis it should not be excised, although malign. First line depicts pathological diagnosis which found the lesion as m for malign and sample label 871. Second line depicts the classifier deep learning recommendation from a −3 to +3 scale and the value of 0.4 would indicate benign. K-Means Sonification and Clinical output was assessed double blinded from classifier and biopsy results. Again there was a discrepancy between Sonifier (−1) and pathology (malign) to Classifier, a 0.40 score of do not excise. There were both activators of benign and malign sounds but the audio determine a malignant lesion. Note a peripheral "Blotch", as described by dermoscopic terms.

Example 10

FIGS. 17A and 17B show different views of the malignant lesion m827. In image A, the first line indicates the audio output from K-Means and found to be malignant (scales from +3 on the left and −3 on the right. The second line indicates that the clinician recommended that the lesion should be excised. The value of Audio is −2 and the clinical review showed a −3 value. FIG. 17B shows a second view wherein the biopsy indicated a malignant lesion. The second line shows the classifier decision and notably it was found not to be malignant but instead benign. The sample is a +0.05. So again there is a discrepancy because audio sonification and pathology (m827) contradicts the classifier which voted DO NOT EXCISE (although close to zero). Cleary the non-invasive audio method concurs with pathology and is more sensitive than the classifier system.

The medical device system and associated method for diagnosing skin lesions by sonification of dermoscopic data have been described in the foregoing description with reference to definite embodiments. It is assumed that various adaptations and adjustments to the referenced embodiments may be made without digressing from the scope of the invention.

Example 11

Figure 18:
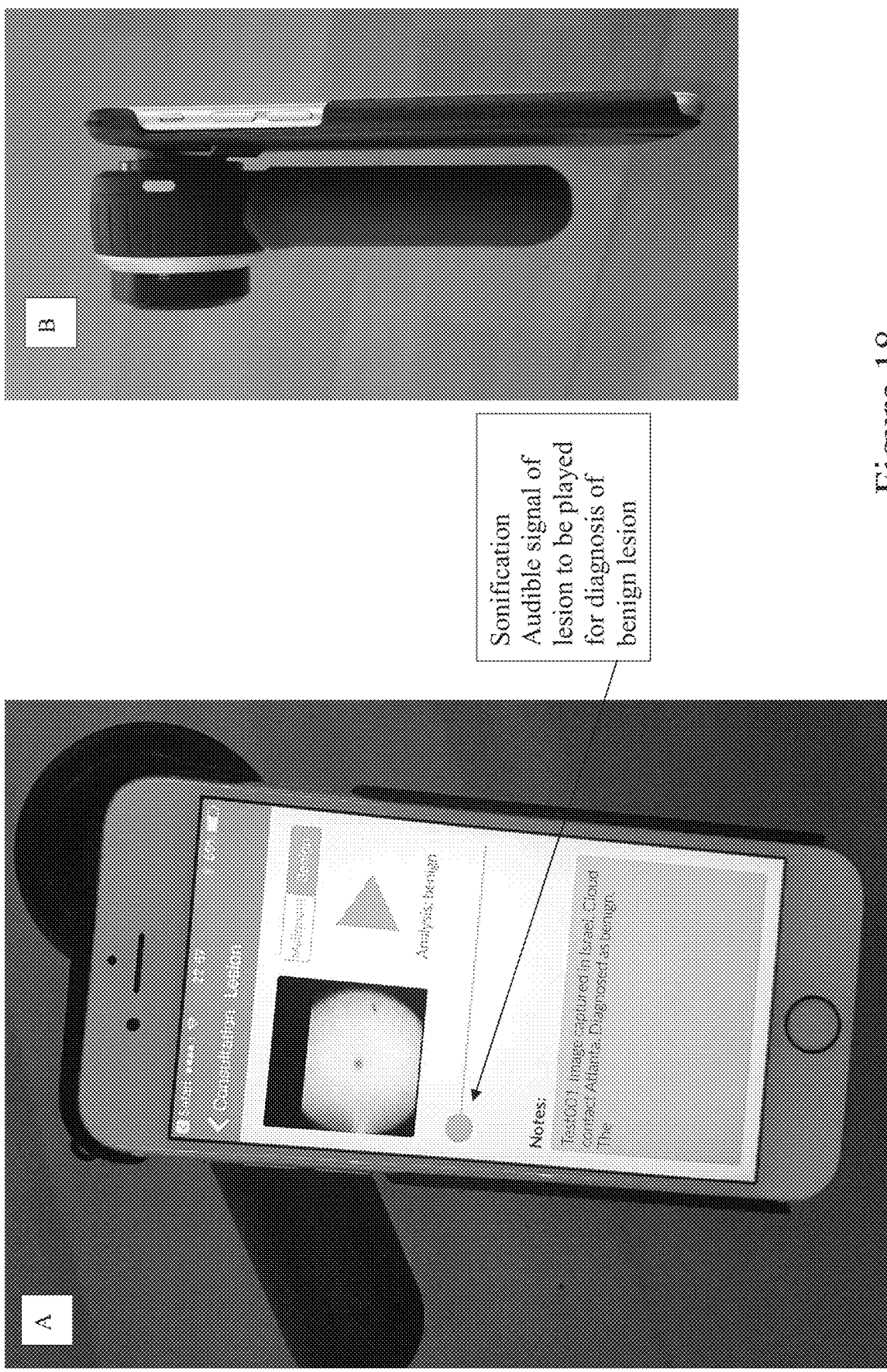
FIG. 18A shows results of testing by an iphone adapted dermoscope (FIG. 18B) to provide a digital photo of a lesion that has been transmitted to a computation center in Atlanta, Ga. to be analyzed using a deep learning computerized system and by sonification to provide an audible output signal sent back to the sender.
Figure 19:
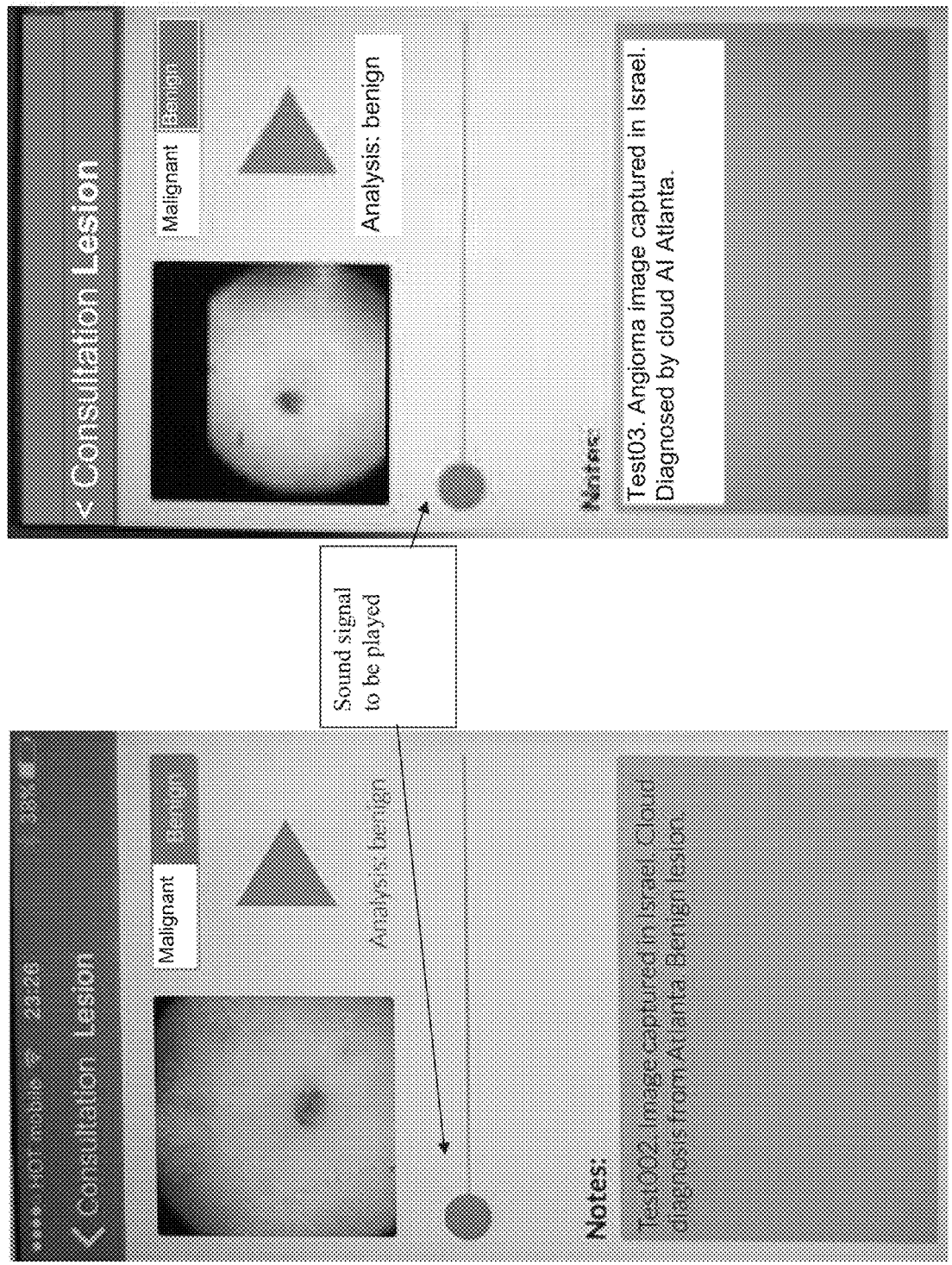
FIGS. 19A and B show additional testing results using the system as shown in FIG. 18.

The present invention includes the use of an optical attachment that turns an iPhone into a digital dermoscope to provide an instantaneous digital photograph of a lesion that could be skin cancer. The digital photo is immediately sent to a server having appropriate computer programs for classifying the digital elements of the lesion and converting such classifications into an audible indication of the diagnosis of the skin lesion. The adapted iphone system shown in FIG. 18B is used for testing wherein a dermoscopic image of a lesion is captured in Tel Aviv, Israel and the image is sent to a cloud controlled deep neuronal network in Atlanta, Ga. In approximately 10 to 12 second the results, shown in FIG. 18A are returned with both a classifier output and a diagnostic sound (sonification) wherein both methods determined that the lesion was benign. Notably the image acquisition of the dermoscope image may be captured as well by voice recognition technology as an alternative to pressing all the buttons for acquiring the image, including the start and play button. The results and output may also be delivered by voice recognition technology. FIG. 19 shows additional testing results using the iphone dermoscope with transmission to the cloud in Atlanta Ga. for conversion to deep learning classifiers and an audible sound by means of a K-means algorithm.

REFERENCES

The contents of all references cited herein are incorporated by reference herein for all purposes.

1. Eggermont A M, Spatz A, Robert C. Cutaneous melanoma. *Lancet.* 2014 Mar. 1; 383 (1919):816-27.
2. Mayer J E, Swetter S M, Teresa Fu, et al. Screening, early detection, education, and trends for melanoma: Current status (2007-2013) and future directions: Part I. Epidemiology, high-risk groups, clinical strategies, and diagnostic technology. *Journal of the American Academy of Dermatology* Volume 71, Issue 4, October 2014, Pages 599. e1-e12.
3. Siegel R, Naishadham D, Jemal A. Cancer statistics, 2012. CA *Cancer J Clin.* 2012 January-February; 62(1): 10-29.
4. Noor O, Nanda A, Rao B K. A dermoscopy survey to assess who is using it and why it is or is not being used. *Int J Dermatol.* 2009 September; 48(9): 951-2.
5. Tsao H, Olazagasti J M, Cordoro K M, et al. Early detection of melanoma: reviewing the ABCDEs. American Academy of Dermatology Ad Hoc Task Force for the ABCDEs of Melanoma, *J Am Acad Dermatol.* 2015 April; 72(4): 717-23.
6. Campos-do-Carmo G, Ramos-e-Silva M. Dermoscopy: basic concepts. *Int J Dermatol.* 2008 July; 47(7): 712-9.
7. Russo T, Piccolo V, Lallas A. et al, Dermoscopy of Malignant Skin Tumours: What's New? Dermatology. 2017: May 10.
8. Ferris L K, Harris R J. New diagnostic aids for melanoma. *Dermatol Clin.* 2012 July; 30(3): 535-45.
9. Annessi G, Bono R, Sampogna F, et al. Sensitivity, specificity, and diagnostic accuracy of three dermoscopic algorithmic methods in the diagnosis of doubtful melanocytic lesions: the importance of light brown structureless areas in differentiating atypical melanocytic nevi from thin melanomas. *J Am Acad Dermatol.* 2007 May; 56(5): 759-67.
10. Bramão I, Reis A, Petersson K M, Faisca L. The role of color information on object recognition: a review and meta-analysis. *Acta Psychol.* 2011 September; 138(1): 244-53.
11. Miller G A. The magical number seven plus or minus two: some limits on our capacity for processing information. *Psychol Rev.* 1956 March; 63(2): 81-97.
12. Skvara H, Teban L, Fiebiger M et al. Limitations of Dermoscopy in the Recognition of Melanoma. *Arch Dermatol.* 2005; 141(2): 155-160.8.
13. Tschandl P, Hofmann L, Fink C3, et al. Melanomas vs. nevi in high-risk patients under long-term monitoring with digital dermatoscopy: do melanomas and nevi already differ at baseline. *J Eur Acad Dermatol Venereol.* 2016 Nov. 29. doi: 10.1111/jdv.14065.
14. Quigley E A, Tokay B A, Jewell S T et al. Technology and Technique Standards for Camera-Acquired Digital Dermatologic Images: A Systematic Review. *JAMA Dermatol.* 2015 May 13.
15. Riccolo D, Ferrari A, Peris K, et al. Dermoscopic diagnosis by a trained clinician vs. a clinician with minimal dermoscopy training vs. computer-aided diagnosis of 341 pigmented skin lesions: a comparative study. *Br J Dermatol.* 2002 September; 147(3): 481-6.
16. Foner L N. Artificial synesthesia via sonification: A wearable augmented sensory system. *Mobile Networks and Applications* 4 (1999) 75-81.
17. Haniffa M A, Lloyd J J, Lawrence C M. The use of a spectrophotometric intracutaneous analysis device in the real-time diagnosis of melanoma in the setting of a melanoma screening clinic. *Br J Dermatol.* 2007 June; 156(6): 1350-2.
18. Monheit G, Cognetta A B, Ferris L et al. The performance of MelaFind: a prospective multicenter study. *Arch Dermatol.* 2011 February; 147(2): 188-94.
19. Marzuka A G, and Book S E, Basal Cell Carcinoma: Pathogenesis, Epidemiology, Clinical Features, Diagnosis, Histopathology, and Management. *Yale J Biol Med.* 2015 June; 88(2): 167-179.
20. Ratushny V, Gober M D, Hick R, et al. From keratinocyte to cancer: the pathogenesis and modeling of cutaneous squamous cell carcinoma. *J Clin Invest.* 2012 Feb. 1; 122(2): 464-472.

21. Borst J G, Soria van Hoeve J. The calyx of Held synapse: from model synapse to auditory relay. *Annu Rev Physiol.* 2012; 74: 199-224.

22. Alais D, Carlile S. Proc Synchronizing to real events: subjective audiovisual alignment scales with perceived auditory depth and speed of sound. *Natl Acad Sci USA.* 2005 Feb. 8; 102(6): 2244-7.

23. King A J. Multisensory Integration: Strategies for Synchronization. *Current Biology*, Volume 15, Issue 9, 10 May 2005, Pages R339-R341.

24. Gaizauskas, B R. The Harmony of the Spheres. *Journal of the Royal Astronomical Society of Canada*, Vol. 68, p.146.

25. Neuhoff J G, Kramer G, Wayand J. Pitch and loudness interact in auditory displays: can the data get lost in the map. *J Exp Psychol Appl.* 2002 March; 8(1):17-25.

26. Han Y C, Han B. Pattern Sonification as a New Timbral Expression. *Leonardo Music Journal*, Volume 24, 2014, pp. 41-43.

27. Scholz D S, Wu L, Pirzer J, et al Sonification as a possible stroke rehabilitation strategy. *Front Neurosci.* 2014 Oct. 20; 8: 332.

28. Ahmad A, Adie S G, Wang M, Boppart S A. Sonification of optical coherence tomography data and images. *Opt Express.* 2010 May 10; 18(10): 9934-44.

29. Dubus G and Bresin R. A Systematic Review of Mapping Strategies for the Sonification of Physical Quantities. 2013; 8(12): e82491.

30. AHRQ Publication No. 11-EHC085-EF, Noninvasive Diagnostic Techniques for the Detection of Skin Cancers, September 2011.

Tht which is claimed is:

1. A computer-implemented method of evaluating a surface skin lesion for determining if malignant or non-malignant by developing a digital data map representing the surface skin lesion for conversion to audio signals, the method comprising:
   providing a tissue image of the surface skin lesion;
   generating segmentation of the tissue image using a computer-aided classification system, wherein similar types of tissue or features of the surface skin lesion are grouped into the same segment resulting in a plurality of different segments representing different types of tissue or features;
   classifying each of the plurality of segments to provide a plurality of classified segments;
   applying a clustering process to the classified segments to provide a plurality of clusters, wherein the clustering process comprises use of a K-means algorithm and wherein each cluster has a centroid and a user of the K-means algorithm forces the classified segments into a maximum of 14 centroids; and
   applying a specific audio signal, using sonification techniques, for each of the plurality of clusters to provide an audio output, and optionally a visual image of the audio output, wherein a pitch is assigned to each centroid;
   wherein the audio output or visual image indicate whether the surface skin lesion is malignant or non-malignant.

2. The method of claim 1 wherein the tissue image is obtained using photography, dermos copy, thermography, multiphoton fluorescence microscopy, multiphoton excitation microscopy, optical coherence tomography, or confocal scanning laser microscopy.

3. The method of claim 1, wherein features of the tissue image are extracted from the image and grouped into a plurality of segments for analysis using the computer-aided classification system.

4. The method of claim 3, wherein the classifying step characterizes the tissue in the tissue image using at least one of the features selected from the group of brightness, shape, color, size, and quality of tissue.

5. The method of claim 3, wherein the computer-aided classification system is a convolution Neural Network selected from Googlenet, ENET or Inception.

6. The method of claim 1, wherein the audio signal is selected from the group consisting of different pitch, loudness, timbre, spatialization and temporal patterns of each visual feature to provide a human-interpretable audio output.

7. The method of claim 1, wherein the audio output is audified by headphones, speaker, iphone, or any device that audifies the audio output at a frequency for auditory perception.

8. The method of claim 1, wherein the user of the K-means algorithm chooses a maximum of 8 centroids to 14 centroids.

9. The method according to claim 1, wherein the tissue image is captured by applying electromagnetic or mechanical energy to the surface skin lesion suspected of being malignant;
   capturing reflected and/or refracted electromagnetic or mechanical energy through a dermoscope or microscope or camera for a digital image;
   converting the reflected and/or refracted or acquired energy into the visual image.

10. The method of claim 1, further comprising converting the audio output to a visual representation.

11. The method of claim 1, further comprising reviewing the audio signal to provide guidance for excising the surface skin tissue suspected of being malignant, wherein the surface skin tissue suspected of being malignant is subsequently excised.

12. The method of claim 1, wherein the sonification techniques comprise a parameter mapping sonification method of centroids.

13. The method of claim 1, wherein the surface skin lesion is an atypical melanocytic hyperplasia, an atypical mole, a dysplastic mole, a cancerous skin disease, actinic keratosis, a basal cell carcinoma or a squamous cell carcinoma.

14. The method of claim 1, wherein the malignant lesions sound comparatively more loud, sharp, or urgent than benign lesions.

15. The method of claim 1, wherein the segmentation of the tissue image comprises pixel segmentation.

* * * * *

UNITED STATES PATENT AND TRADEMARK OFFICE
CERTIFICATE OF CORRECTION

| | | |
|---|---|---|
| PATENT NO. | : 11,484,247 B2 | |
| APPLICATION NO. | : 16/311372 | |
| DATED | : November 1, 2022 | |
| INVENTOR(S) | : Avi Dascalu | |

It is certified that error appears in the above-identified patent and that said Letters Patent is hereby corrected as shown below:

In the Claims

Column 22, Claim 2, Line 4 should read:
- obtained using photography, dermoscopy, thermography, -

Signed and Sealed this
Seventh Day of February, 2023

Katherine Kelly Vidal
*Director of the United States Patent and Trademark Office*